(12) United States Patent
Tanzer et al.

(10) Patent No.: US 6,723,529 B2
(45) Date of Patent: Apr. 20, 2004

(54) METHODS FOR THE IDENTIFICATION OF INHIBITORS OF α-AMINOADIPATE REDUCTASE AS ANTIBIOTICS

(75) Inventors: Matthew M. Tanzer, Durham, NC (US); Jeffrey Shuster, Chapel Hill, NC (US); Lisbeth Hamer, Durham, NC (US); Kiichi Adachi, Durham, NC (US); Todd M. DeZwaan, Apex, NC (US); Sze-Chung Lo, Durham, NC (US); Maria Victoria Montenegro-Chamorro, Morrisville, NC (US); Sheryl Frank, Durham, NC (US); Blaise Darveaux, Hillsborough, NC (US); Sanjoy K. Mahanty, Chapel Hill, NC (US); Ryan Heiniger, Raleigh, NC (US); Amy Skalchunes, Raleigh, NC (US); Huaqin Pan, Apex, NC (US); Rex Tarpey, Apex, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 10/011,146

(22) Filed: Nov. 9, 2001

(65) Prior Publication Data

US 2003/0104511 A1 Jun. 5, 2003

(51) Int. Cl.⁷ .............................. C12Q 1/04; C12Q 1/26; C12Q 1/18
(52) U.S. Cl. .............................. 435/34; 435/25; 435/32; 530/300
(58) Field of Search ........................ 435/25, 24, 32, 435/29, 23

(56) References Cited

U.S. PATENT DOCUMENTS

| | | | |
|---|---|---|---|
| 4,920,109 A | 4/1990 | Onishi et al. | 514/171 |
| 4,920,111 A | 4/1990 | Onishi et al. | 514/171 |
| 4,920,112 A | 4/1990 | Onishi et al. | 514/171 |
| 4,920,113 A | 4/1990 | Onishi et al. | 514/171 |
| 4,921,844 A | 5/1990 | Onishi et al. | 514/171 |
| 5,976,848 A | 11/1999 | Davis et al. | 435/183 |
| 6,074,830 A | 6/2000 | Bacot et al. | 435/6 |

FOREIGN PATENT DOCUMENTS

WO    WO 00/00643    \*    1/2000

OTHER PUBLICATIONS

Aufauvre–Brown, Agnes et al., "*Aspergillus fumigatus chsE:* A Gene Related to CHS3 of *Saccharomyces cerevisiae* and Important for Hyphal Growth and Conidiophore Development but Not Pathogenicity." Fungal Genetics and Biology (1997) 21: 141–152.

Tang, Christoph M. et al., "Virulence Studies of *Aspergillus nidulans* Mutants Requiring Lysine or p–Aminobenzoic Acid in Invasive Pulmonary Aspergillosis." Infection and Immunity (Dec. 1994) : 5255–5260.

Brown, Jeremy S. et al., "Signature–tagged and directed mutagenesis identify PABA synthetase as essential for *Aspergillus fumigatus* pathocenicity." Molecular Microbiology (2000) 36(6): 1371–1380.

(List continued on next page.)

*Primary Examiner*—Louise N. Leary
(74) *Attorney, Agent, or Firm*—Deborah H. Spencer; Timothy G. Hofmeyer; Laura L. Kiefer

(57) ABSTRACT

The present inventors have discovered that α-Aminoadipate Reductase is essential for fungal pathogenicity. Specifically, the inhibition of α-Aminoadipate Reductase gene expression in fungi results in no signs of successful infection or lesions. Thus, α-Aminoadipate Reductase can be used as a target for the identification of antibiotics, preferably antifungals. Accordingly, the present invention provides methods for the identification of compounds that inhibit α-Aminoadipate Reductase expression or activity. The methods of the invention are useful for the identification of antibiotics, preferably antifungals.

40 Claims, 3 Drawing Sheets

L-2-Aminoadipate + NADPH + ATP

α-*Aminoadipate Reductase* + $Mg^{2+}$

Figure 1:
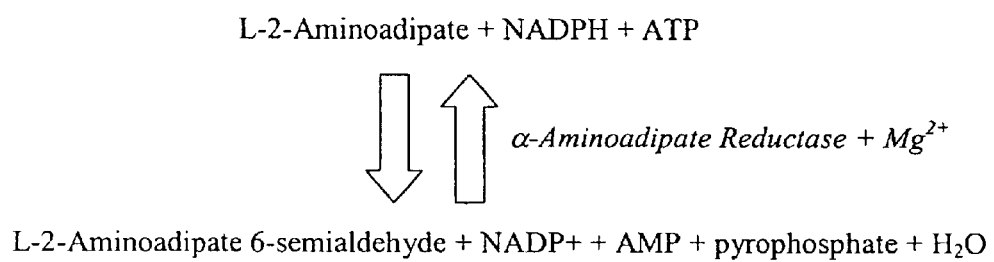
Figure 2:
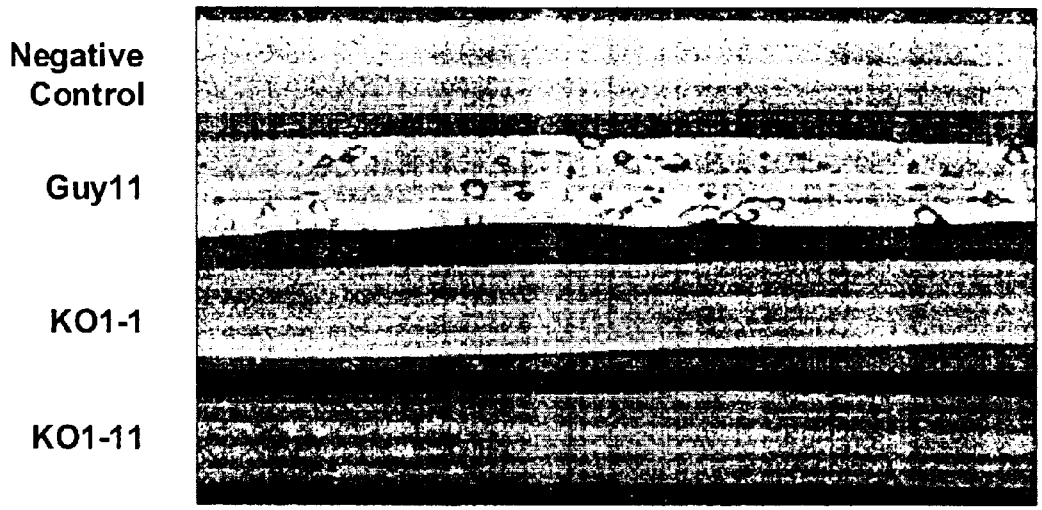
Figure 3A:
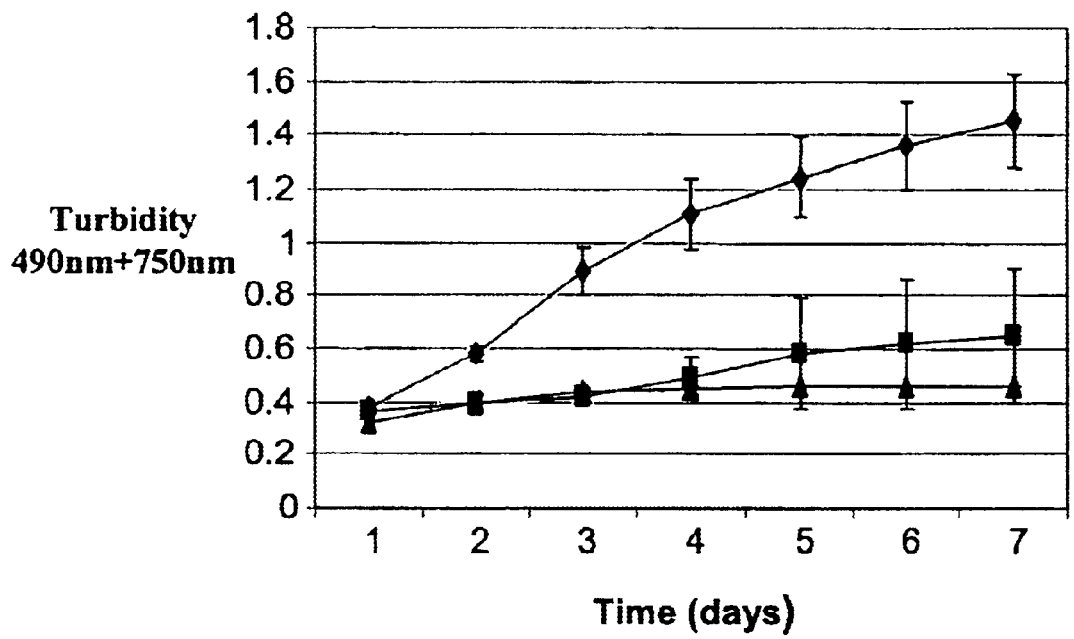
Figure 3B:
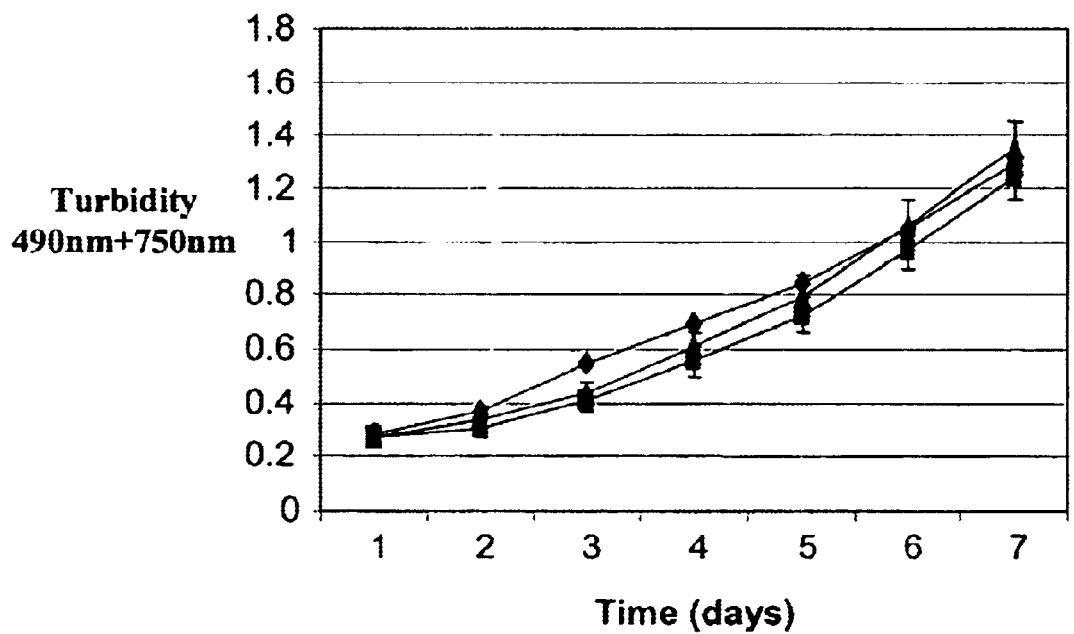

L-2-Aminoadipate 6-semialdehyde + $NADP+$ + AMP + pyrophosphate + $H_2O$

OTHER PUBLICATIONS

D'Enfert, Christophe. et al, "Attenuated Virulence of Uridine–Uracil Auxtrophs of *Aspergillus fumigatus*." Infection and Immunity (Oct. 1996) : 4401–4405.

Hensel, M. et al,"The role of the *Asperigillus fumigatus* areA gene in invasive pulmonary aspergillosis." Mol Gen enet (1998): 553–557.

Shibuya, Kazutoshi et al., "Histophathology of experimental invasive pulmonary aspergillosis in rats: Pathological comparison of pulmonary lesions induced by specific virulent factor deficient mutants." Microbial Pathogenesis (1999) 27: 123–131.

Smith, Joanne M. et al., "Virulence of *Aspergillus fumigatus* Double Mutants Lacking Restrictocin and an Alkaline Protease in a Low–Dose Model of Invasive Pulmonary Apergillosis." Infection and Immunity (Dec. 1994) : 5247–5254.

Reichard U. et al, Virulence of an aspergillopepsin–deficient mutant of *Aspergillus fumigatus* and evidence for another aspartic proteinase linked to the fungal cell wall. J Med Vet Mycol (May–Jun. 1997) ; 35 (3): 189–96.

Hijarrubia, M. J. et al., "Characterization of the lys2 gene *Acremonium chrysogenum* encoding a functional α–aminoadipate activating and reducing enzyme." Mol Gen Genet (2001) 264: 755–762.

Ford, Richard et al., "Molecular properties of the lysl1+ gene and the regulation of α–aminoadipate reductase in *Schizosaccharomyces pombe*." Curr Genet (1995) 28: 131–137.

Nishida, Hiromi et al., "What is the Characteristic of Fungal Lysine Synthesis through the α–Aminoapidate Pathway?" J Mol Evol (2000) 51: 299–302.

Casquerio, J. et al., "Characterization of the lyse2 gene of *Penicillium chrysogenum* encoding α–aminoadipic acid reductase." Mol Gen Genet (1998) 259: 549–556.

Bleykasten–Grosshans, Claudine et al., "Cloning and sequence of the LYS2 homologue gene from the osmotolerant yeast *Pichia sorbitophila*." Yeast (2001) 18: 16–67.

Bhattacharjee, V. et al., "Characterization of a double gene disruption in the LYS2 locus of the pathogenic yeast, *Candida albicans*." Medical Mycology (1999) 37: 411–417.

Morris, Mary E. et al., "Nucleotide sequence of the LYS2 gene of *Saccharomyces cerevisiae*: homology to *Bacillus brevis* tryocidein sythetase 1." Gene, (1991) 98: 141–145.

Suvarna, Kalavati et al., "Molecular analysis of the LYS2 gene of *Candida albicans*: homology to peptide antibiotic synthetaseand the regulation of the α–aminoadipate reductase." Curr Genet, (1998) 33: 268–275.

Tucci, Anthony et al., "Control of Lysine Biosynthesis in Yeast." Archives of Biochemistry and Biophysics, (1972) 153:751–754.

* cited by examiner

METHODS FOR THE IDENTIFICATION OF INHIBITORS OF α-AMINOADIPATE REDUCTASE AS ANTIBIOTICS

FIELD OF THE INVENTION

The invention relates generally to methods for the identification of antibiotics, preferably antifungals that affect the biosynthesis of lysine. This application is co-pending with our application entitled "Methods for the Identification of Inhibitors of Homocitrate Synthase as Antibiotics".

BACKGROUND OF THE INVENTION

Filamentous fungi are the causal agents responsible for many serious pathogenic infections of plants and animals. Since fungi are eukaryotes, and thus more similar to their host organisms than, for example bacteria, the treatment of infections by fungi poses special risks and challenges not encountered with other types of infections. One such fungus is *Magnaporthe grisea*, the fungus that causes rice blast disease. It is an organism that poses a significant threat to food supplies worldwide. Other examples of plant pathogens of economic importance include the pathogens in the genera Agaricus, Alternaria, Anisogramma, Anthracoidea, Antrodia, Apiognomonia, Apiosporina, Armillaria, Ascochyta, Aspergillus, Bipolaris, Bjerkandera, Botryosphaeria, Botrytis, Ceratobasidium, Ceratocystis, Cercospora, Cercosporidium, Cerotelium, Cerrena, Chondrostereum, Chryphonectria, Chrysomyxa, Cladosporium, Claviceps, Cochliobolus, Coleosporium, Colletotrichium, Colletotrichum, Corticium, Corynespora, Cronartium, Cryphonectria, Cryptosphaeria, Cyathus, Cymadothea, Cytospora, Daedaleopsis, Diaporthe, Didymella, Diplocarpon, Diplodia, Discohainesia, Discula, Dothistroma, Drechslera, Echinodontium, Elsinoe, Endocronartium, Endothia, Entyloma, Epichloe, Erysiphe, Exobasidium, Exserohilum, Fomes, Fomitopsis, Fusarium, Gaeumannomyces, Ganoderma, Gibberella, Gloeocercospora, Gloeophyllum, Gloeoporus, Glomerella, Gnomoniella, Guignardia, Gymnosporangium, Helminthosporium, Herpotrichia, Heterobasidion, Hirschioporus, Hypodermella, Inonotus, Irpex, Kabatiella, Kabatina, Laetiporus, Laetisaria, Lasiodiplodia, Laxitextum, Leptographium, Leptosphaeria, Leptosphaerulina, Leucytospora, Linospora, Lophodermella, Lophodermium, Macrophomina, Magnaporthe, Marssonina, Melampsora, Melampsorella, Meria, Microdochium, Microsphaera, Monilinia, Monochaetia, Morchella, Mycosphaerella, Myrothecium, Nectria, Nigrospora, Ophiosphaerella, Ophiostoma, Penicillium, Perenniporia, Peridermium, Pestalotia, Phaeocryptopus, Phaeolus, Phakopsora, Phellinus, Phialophora, Phoma, Phomopsis, Phragmidium, Phyllachora, Phyllactinia, Phyllosticta, Phymatotrichopsis, Pleospora, Podosphaera, Pseudopeziza, Pseudoseptoria, Puccinia, Pucciniastrum, Pyricularia, Rhabdocline, Rhizoctonia, Rhizopus, Rhizosphaera, Rhynchosporium, Rhytisma, Schizophyllum, Schizopora, Scirrhia, Sclerotinia, Sclerotium, Scytinostroma, Septoria, Setosphaera, Sirococcus, Spaerotheca, Sphaeropsis, Sphaerotheca, Sporisorium, Stagonospora, Stemphylium, Stenocarpella, Stereum, Taphrina, Thielaviopsis, Tilletia, Trametes, Tranzschelia, Trichoderma, Tubakia, Typhula, Uncinula, Urocystis, Uromyces, Ustilago, Valsa, Venturia, Verticillium, Xylaria, and others. Related organisms in the classification, oomycetes, that include the genera Albugo, Aphanomyces, Bremia, Peronospora, Phytophthora, Plasmodiophora, Plasmopara, Pseudoperonospora, Pythium, Sclerophthora, and others are also significant plant pathogens and are sometimes classified along with the true fungi. Human diseases that are caused by filamentous fungi include life-threatening lung and disseminated diseases, often a result of infections by *Aspergillus fumigatus*. Other fungal diseases in animals are caused by fungi in the genera, Fusarium, Blastomyces, Microsporum, Trichophyton, Epidermophyton, Candida, Histoplamsa, Pneumocystis, Cryptococcus, other Aspergilli, and others. The control of fungal diseases in plants and animals is usually mediated by chemicals that inhibit the growth, proliferation, and/or pathogenicity of the fungal organisms. To date, there are less than twenty known modes-of-action for plant protection fungicides and human antifungal compounds.

A pathogenic organism has been defined as an organism that causes, or is capable of causing disease. Pathogenic organisms propagate on or in tissues and may obtain nutrients and other essential materials from their hosts. A substantial amount of work concerning filamentous fungal pathogens has been performed with the human pathogen, *Aspergillus fumigatus*. Shibuya et al. (Shibuya, K., M. Takaoka, et al (1999) Microb Pathog 27: 123–31 (PMID: 10455003)) have shown that the deletion of either of two suspected pathogenicity related genes encoding an alkaline protease or a hydrophobin (rodlet) respectively, did not reduce mortality of mice infected with these mutant strains. Smith et al. (Smith, J. M., C. M. Tang, et al. (1994) Infect Immun 62: 5247–54 (PMID: 7960101)) showed similar results with alkaline protease and the ribotoxin restrictocin; *Aspergillus fumigatus* strains mutated for either of these genes were fully pathogenic to mice. Reichard et al. (Reichard, U., M. Monod, et al. (1997) J Med Vet Mycol 35: 189–96 (PMID: 9229335)) showed that deletion of the suspected pathogenicity gene encoding, aspergillopepsin (PEP) in *Aspergillus fumigatus*, had no effect on mortality in a guinea pig model system, and Aufauvre-Brown et al (Aufauvre-Brown, A., E. Mellado, et al. (1997) Fungal Genet Biol 21: 141–52 (PMID: 9073488)) showed no effects of a chitin synthase mutation on pathogenicity. However, not all experiments produced negative results. Ergosterol is an important membrane component found in fungal organisms. Pathogenic fungi that lack key enzymes in this biochemical pathway might be expected to be non-pathogenic since neither the plant nor animal hosts contain this particular sterol. Many antifungal compounds that affect this biochemical pathway have been described (Onishi, J. C. and A. A. Patchett (1990a, b, c, d, and e) U.S. Pat. Nos. 4,920,109; 4,920,111; 4,920,112; 4,920,113; and 4,921,844, Merck & Co. Inc. (Rahway N.J.)) and (Hewitt, H. G. (1998) *Fungicides in Crop Protection* Cambridge, University Press). D'Enfert et al. (D'Enfert, C., M. Diaquin, et al. (1996) Infect Immun 64: 4401–5 (PMID: 8926121)) showed that an *Aspergillus fumigatus* strain mutated in an orotidine 5'-phosphate decarboxylase gene was entirely non-pathogenic in mice, and Brown et al. (Brown, J. S., A. Aufauvre-Brown, et al. (2000) Mol Microbiol 36: 1371–80 (PMID: 10931287)) observed a non-pathogenic result when genes involved in the synthesis of para-aminobenzoic acid were mutated. Some specific target genes have been described as having utility for the screening of inhibitors of plant pathogenic fungi. Bacot et al. (Bacot, K. O., D. B. Jordan, et al. (2000) U.S. Pat. No. 6,074,830, E. I. du Pont de Nemours & Company (Wilmington Del.)) describe the use of 3,4-dihydroxy-2-butanone 4-phosphate synthase, and Davis et al. (Davis, G. E., G. D. Gustafson, et al. (1999) U.S. Pat. No. 5,976,848, Dow AgroSciences LLC (Indianapolis Ind.)) describe the use of dihydroorotate dehydrogenase for potential screening purposes.

There are also a number of papers that report less clear results, showing neither fill pathogenicity nor non-pathogenicity of mutants. Hensel et al. (Hensel, M., H. N. Arst, Jr., et al. (1998) Mol Gen Genet 258: 553–7 (PMID: 9669338)) showed only moderate effects of the deletion of the areA transcriptional activator on the pathogenicity of *Aspergillus fumigatus*. Tang et al. (Tang, C. M., J. M. Smith, et al. (1994) Infect Immun 62: 5255–60 (PMID: 7960102)) using the related fungus, *Aspergillus nidulans,* observed that a mutation in para-aminobenzoic acid synthesis prevented mortality in mice, while a mutation in lysine biosynthesis had no significant effect on the mortality of the infected mice.

Therefore, it is not currently possible to determine which specific growth materials may be readily obtained by a pathogen from its host, and which materials may not. Surprising, especially in light of the results showing that a lysine biosynthesis mutation in the filamentous fungus, *Aspergillus nidulans,* had no significant effect on the pathogenicity in a mouse model system (Tang, C. M., J. M. Smith, et al. (1994) Infect Immun 62: 5255–60 (PMID: 7960102)), we have found that *Magnaporthe grisea* that cannot synthesize their own lysine are entirely non-pathogenic on their host organism. To date there do not appear to be any publications demonstrating an anti-pathogenic effect of the knock-out, over-expression, antisense expression, or inhibition of the genes or gene products involved in lysine biosynthesis in filamentous fungi. Thus, it has not been shown that the de novo biosynthesis of lysine is essential for fungal pathogenicity. Our co-pending application entitled “Methods for the Identification of Inhibitors of Homocitrate Synthase as Antibiotics” shows that the disruption of lysine biosynthesis as the result of a disruption of the gene encoding the enzyme activity, homocitrate synthase, also results in a non-pathogenic phenotype for *M. grisea*. Thus, it would be desirable to determine the utility of the enzymes involved in lysine biosynthesis for evaluating antibiotic compounds, especially fungicides. If a fungal biochemical pathway or specific gene product in that pathway is shown to be required for fungal pathogenicity, various formats of in vitro and in vivo screening assays may be put in place to discover classes of chemical compounds that react with the validated target gene, gene product, or biochemical pathway, and are thus candidates for antifungal, biocide, and biostatic materials.

SUMMARY OF THE INVENTION

Surprisingly, the present inventors have discovered that in vivo disruption of the gene encoding α-Aminoadipate Reductase in *Magnaporthe grisea* prevents or inhibits the pathogenicity of the fungus. Thus, the present inventors have discovered that α-Aminoadipate Reductase is essential for normal rice blast pathogenicity, and can be used as a target for the identification of antibiotics, preferably fungicides. Accordingly, the present invention provides methods for the identification of compounds that inhibit α-Aminoadipate Reductase expression or activity. The methods of the invention are useful for the identification of antibiotics, preferably fungicides.

BRIEF DESCRIPTION OF THE FIGURES

FIG. 1 shows the reaction performed by α-Aminoadipate Reductase (AAR1) reaction. The Substrates/Products are L-2-Aminoadipate+NADPH+ATP and the Products/Substrates are L-2-Aminoadipate 6-semialdehyde+NADP++AMP+pyrophosphate+$H_2O$. The function of the α-Aminoadipate Reductase enzyme is the interconversion of L-2-Aminoadipate, NADPH, and ATP to L-2-Aminoadipate 6-semialdehyde, NADP+, AMP, pyrophosphate, and $H_2O$. This reaction is part of the lysine biosynthesis pathway.

FIG. 2 shows a digital image showing the effect of AAR1 gene disruption on *Magnaporthe grisea* pathogenicity using whole plant infection assays. Rice variety CO39 was inoculated with wild-type and the transposon insertion strains, KO1-1 and KO1-11. Leaf segments were imaged at five days post-inoculation.

FIG. 3. Verification of Gene Function by Analysis of Nutritional Requirements. Wild-type and transposon insertion strains, KO1-1 and KO1-11, were grown in (A) minimal media and (B) minimal media with the addition of L-lysine, respectively. The x-axis shows time in days and the y-axis shows turbidity measured at 490 nanometers and 750 nanometers. The symbols represent wildtype (--♦--), transposon strain KO1-1 (--■--), and transposon strain KO1-11 (--▲--).

DETAILED DESCRIPTION OF THE INVENTION

Unless otherwise indicated, the following terms are intended to have the following meanings in interpreting the present invention.

The term “active against” in the context of compounds, agents, or compositions having antibiotic activity indicates that the compound exerts an effect on a particular target or targets which is deleterious to the in vitro and/or in vivo growth of an organism having that target or targets. In particular, a compound active against a gene exerts an action on a target which affects an expression product of that gene. This does not necessarily mean that the compound acts directly on the expression product of the gene, but instead indicates that the compound affects the expression product in a deleterious manner. Thus, the direct target of the compound may be, for example, at an upstream component which reduces transcription from the gene, resulting in a lower level of expression. Likewise, the compound may affect the level of translation of a polypeptide expression product, or may act on a downstream component of a biochemical pathway in which the expression product of the gene has a major biological role. Consequently, such a compound can be said to be active against the gene, against the gene product, or against the related component either upstream or downstream of that gene or expression product. While the term “active against” encompasses a broad range of potential activities, it also implies some degree of specificity of target. Therefore, for example, a general protease is not “active against” a particular gene which produces a polypeptide product. In contrast, a compound which inhibits a particular enzyme is active against that enzyme and against the gene which codes for that enzyme.

As used herein, the term “allele” refers to any of the alternative forms of a gene that may occur at a given locus.

As used herein, the term “α-Aminoadipate Reductase (EC 1.2.1.31), α-Aminoadipate Reductase polypeptide, α-Aminoadipate semialdehyde dehydrogenase, or Alpha-Aminoadipate Reductase” is synonymous with “the AAR1 gene product” or the “the ASD1 gene product” and refers to an enzyme that catalyses the interconversion of L-2-Aminoadipate, NADPH, and ATP with L-2-Aminoadipate 6-semialdehyde, NADP+, AMP, pyrophosphate, and $H_2O$.

The term “antibiotic” refers to any substance or compound that when contacted with a living cell, organism, virus, or other entity capable of replication, results in a reduction of growth, viability, or pathogenicity of that entity.

The term "binding" refers to a non-covalent or a covalent interaction, preferably non-covalent, that holds two molecules together. For example, two such molecules could be an enzyme and an inhibitor of that enzyme. Non-covalent interactions include hydrogen bonding, ionic interactions among charged groups, van der Waals interactions and hydrophobic interactions among nonpolar groups. One or more of these interactions can mediate the binding of two molecules to each other.

The term "biochemical pathway" or "pathway" refers to a connected series of biochemical reactions normally occurring in a cell, or more broadly a cellular event such as cellular division or DNA replication. Typically, the steps in such a biochemical pathway act in a coordinated fashion to produce a specific product or products or to produce some other particular biochemical action. Such a biochemical pathway requires the expression product of a gene if the absence of that expression product either directly or indirectly prevents the completion of one or more steps in that pathway, thereby preventing or significantly reducing the production of one or more normal products or effects of that pathway. Thus, an agent specifically inhibits such a biochemical pathway requiring the expression product of a particular gene if the presence of the agent stops or substantially reduces the completion of the series of steps in that pathway. Such an agent, may, but does not necessarily, act directly on the expression product of that particular gene.

As used herein, the term "cDNA" means complementary deoxyribonucleic acid.

As used herein, the term "CoA" means coenzyme A.

As used herein, the term "conditional lethal" refers to a mutation permitting growth and/or survival only under special growth or environmental conditions.

As used herein, the term "cosmid" refers to a hybrid vector, used in gene cloning, that includes a cos site (from the lambda bacteriophage). It also contains drug resistance marker genes and other plasmid genes. Cosmids are especially suitable for cloning large genes or multigene fragments.

As used herein, the term "dominant allele" refers to a dominant mutant allele in which a discernable mutant phenotype can be detected when this mutation is present in an organism that also contains a wild type (non-mutant), recessive allele, or other dominant allele.

As used herein, the term "DNA" means deoxyribonucleic acid.

As used herein, the term "ELISA" means enzyme-linked immunosorbent assay.

"Fungi" (singular: fungus) refers to whole fungi, fungal organs and tissues (e.g., asci, hyphae, pseudohyphae, rhizoid, sclerotia, sterigmata, spores, sporodochia, sporangia, synnemata, conidia, ascostroma, cleistothecia, mycelia, perithecia, basidia and the like), spores, fungal cells and the progeny thereof. Fungi are a group of organisms (about 50,000 known species), including, but not limited to, mushrooms, mildews, moulds, yeasts, etc., comprising the kingdom Fungi. They can either exist as single cells or make up a multicellular body called a mycelium, which consists of filaments known as hyphae. Most fungal cells are multinucleate and have cell walls, composed chiefly of chitin. Fungi exist primarily in damp situations on land and, because of the absence of chlorophyll and thus the inability to manufacture their own food by photosynthesis, are either parasites on other organisms or saprotrophs feeding on dead organic matter. The principal criteria used in classification are the nature of the spores produced and the presence or absence of cross walls within the hyphae. Fungi are distributed worldwide in terrestrial, freshwater, and marine habitats. Some live in the soil. Many pathogenic fungi cause disease in animals and man or in plants, while some saprotrophs are destructive to timber, textiles, and other materials. Some fungi form associations with other organisms, most notably with algae to form lichens.

As used herein, the term "fungicide", "antifungal", or "antimycotic" refers to an antibiotic substance or compound that kills or suppresses the growth, viability, or pathogenicity of at least one fungus, fungal cell, fungal tissue or spore.

In the context of this disclosure, "gene" should be understood to refer to a unit of heredity. Each gene is composed of a linear chain of deoxyribonucleotides which can be referred to by the sequence of nucleotides forming the chain. Thus, "sequence" is used to indicate both the ordered listing of the nucleotides which form the chain, and the chain, itself, which has that sequence of nucleotides. ("Sequence" is used in the similar way in referring to RNA chains, linear chains made of ribonucleotides.) The gene may include regulatory and control sequences, sequences which can be transcribed into an RNA molecule, and may contain sequences with unknown function. The majority of the RNA transcription products are messenger RNAs (mRNAs), which include sequences which are translated into polypeptides and may include sequences which are not translated. It should be recognized that small differences in nucleotide sequence for the same gene can exist between different fungal strains, or even within a particular fungal strain, without altering the identity of the gene.

As used in this disclosure, the terms "growth" or "cell growth" of an organism refers to an increase in mass, density, or number of cells of said organism. Some common methods for the measurement of growth include the determination of the optical density of a cell suspension, the counting of the number of cells in a fixed volume, the counting of the number of cells by measurement of cell division, the measurement of cellular mass or cellular volume, and the like.

As used in this disclosure, the term "growth conditional phenotype" indicates that a fungal strain having such a phenotype exhibits a significantly greater difference in growth rates in response to a change in one or more of the culture parameters than an otherwise similar strain not having a growth conditional phenotype. Typically, a growth conditional phenotype is described with respect to a single growth culture parameter, such as temperature. Thus, a temperature (or heat-sensitive) mutant (i.e., a fungal strain having a heat-sensitive phenotype) exhibits significantly different growth, and preferably no growth, under non-permissive temperature conditions as compared to growth under permissive conditions. In addition, such mutants preferably also show intermediate growth rates at intermediate, or semi-permissive, temperatures. Similar responses also result from the appropriate growth changes for other types of growth conditional phenotypes.

As used herein, the term "$H_2O$" means water.

As used herein, the term "AAR1" means a gene encoding α-Aminoadipate Reductase activity, referring to an enzyme that catalyses the interconversion of L-2-Aminoadipate, NADPH, and ATP with L-2-Aminoadipate 6-semialdehyde, NADP+, AMP, pyrophosphate, and $H_2O$.

As used herein, the term "heterologous AAR1 gene" means a gene, not derived from *Magnaporthe grisea,* and having: at least 50% sequence identity, preferably 60%, 70%, 80%, 90%, 95%, 99% sequence identity and each integer unit of sequence identity from 50–100% in ascending order to SEQ ID NO: 1 or SEQ ID NO: 2; or at least 10% of the activity of a *Magnaporthe grisea* α-Aminoadipate Reductase, preferably 25%, 50%, 75%, 90%, 95%, 99% and each integer unit of activity from 10–100% in ascending order.

As used herein, the term "His-Tag" refers to an encoded polypeptide consisting of multiple consecutive histidine amino acids.

As used herein, the term "HPLC" means high pressure liquid chromatography.

As used herein, the terms "hph", "hygromycin B phosphotransferase", and "hygromycin resistance gene" refer to the *E. coli* hygromycin phosphotransferase gene or gene product.

As used herein, the term "hygromycin B" refers to an aminoglycosidic antibiotic, used for selection and maintenance of eukaryotic cells containing the *E. coli* hygromycin resistance gene.

"Hypersensitive" refers to a phenotype in which cells are more sensitive to antibiotic compounds than are wild-type cells of similar or identical genetic background.

"Hyposensitive" refers to a phenotype in which cells are less sensitive to antibiotic compounds than are wild-type cells of similar or identical genetic background.

As used herein, the term "imperfect state" refers to a classification of a fungal organism having no demonstrable sexual life stage.

The term "inhibitor", as used herein, refers to a chemical substance that inactivates the enzymatic activity of α-Aminoadipate Reductase or substantially reduces the level of enzymatic activity, wherein "substantially" means a reduction at least as great as the standard deviation for a measurement, preferably a reduction by 50%, more preferably a reduction of at least one magnitude, i.e. to 10%. The inhibitor may function by interacting directly with the enzyme, a cofactor of the enzyme, the substrate of the enzyme, or any combination thereof.

A polynucleotide may be "introduced" into a fungal cell by any means known to those of skill in the art, including transfection, transformation or transduction, transposable element, electroporation, particle bombardment, infection and the like. The introduced polynucleotide may be maintained in the cell stably if it is incorporated into a non-chromosomal autonomous replicon or integrated into the fungal chromosome. Alternatively, the introduced polynucleotide may be present on an extra-chromosomal non-replicating vector and be transiently expressed or transiently active.

As used herein, the term "knockout" or "gene disruption" refers to the creation of organisms carrying a null mutation (a mutation in which there is no active gene product), a partial null mutation or mutations, or an alteration or alterations in gene regulation by interrupting a DNA sequence through insertion of a foreign piece of DNA. Usually the foreign DNA encodes a selectable marker.

As used herein, the term "LB agar" means Luria's Broth agar.

The term "method of screening" means that the method is suitable, and is typically used, for testing for a particular property or effect in a large number of compounds. Typically, more than one compound is tested simultaneously (as in a 96-well microtiter plate), and preferably significant portions of the procedure can be automated. "method of screening" also refers to determining a set of different properties or effects of one compound simultaneously.

As used herein, the term "mRNA" means messenger ribonucleic acid.

As used herein, the term "mutant form" of a gene refers to a gene which has been altered, either naturally or artificially, changing the base sequence of the gene. The change in the base sequence may be of several different types, including changes of one or more bases for different bases, deletions, and/or insertions, such as by a transposon. By contrast, a normal form of a gene (wild type) is a form commonly found in natural populations of an organism. Commonly a single form of a gene will predominate in natural populations. In general, such a gene is suitable as a normal form of a gene, however, other forms which provide similar functional characteristics may also be used as a normal gene. In particular, a normal form of a gene does not confer a growth conditional phenotype on the strain having that gene, while a mutant form of a gene suitable for use in these methods does provide such a growth conditional phenotype.

As used herein, the term "Ni" refers to nickel.

As used herein, the term "Ni-NTA" refers to nickel sepharose.

As used herein, the term "one form" of a gene is synonymous with the term "gene", and a "different form" of a gene refers to a gene that has greater than 49% sequence identity and less than 100% sequence identity with said first form.

As used herein, the term "pathogenicity" refers to a capability of causing disease. The term is applied to parasitic microorganisms in relation to their hosts.

As used herein, the term "PCR" means polymerase chain reaction.

The "percent (%) sequence identity" between two polynucleotide or two polypeptide sequences is determined according to the either the BLAST program (Basic Local Alignment Search Tool; (Altschul, S. F., W. Gish, et al. (1990) J Mol Biol 215: 403–10 (PMID: 2231712)) at the National Center for Biotechnology or using Smith Waterman Alignment (Smith, T. F. and M. S. Waterman (1981) J Mol Biol 147: 195–7 (PMID: 7265238)) as incorporated into GeneMatcher Plus™. It is understood that for the purposes of determining sequence identity when comparing a DNA sequence to an RNA sequence, a thymine nucleotide is equivalent to a uracil nucleotide.

By "polypeptide" is meant a chain of at least two amino acids joined by peptide bonds. The chain may be linear, branched, circular or combinations thereof. Preferably, polypeptides are from about 10 to about 1000 amino acids in length, more preferably 10–50 amino acids in length. The polypeptides may contain amino acid analogs and other modifications, including, but not limited to glycosylated or phosphorylated residues.

As used herein, the term "proliferation" is synonymous to the term "growth".

As used herein, the term "reverse transcriptase-PCR" means reverse transcription-polymerase chain reaction.

As used herein, the term "RNA" means ribonucleic acid.

As used herein, "semi-permissive conditions" are conditions in which the relevant culture parameter for a particular growth conditional phenotype is intermediate between permissive conditions and non-permissive conditions. Consequently, in semi-permissive conditions an organism having a growth conditional phenotype will exhibit growth rates intermediate between those shown in permissive conditions and non-permissive conditions. In general, such intermediate growth rate may be due to a mutant cellular component which is partially functional under semi-permissive conditions, essentially fully functional under permissive conditions, and is non-functional or has very low function under non-permissive conditions, where the level of function of that component is related to the growth rate of the organism. An intermediate growth rate may also be a result of a nutrient substance or substances that are present in amounts not sufficient for optimal growth rates to be achieved.

"Sensitivity phenotype" refers to a phenotype that exhibits either hypersensitivity or hyposensitivity.

The term "specific binding" refers to an interaction between α-Aminoadipate Reductase and a molecule or compound, wherein the interaction is dependent upon the primary amino acid sequence and/or the conformation of α-Aminoadipate Reductase.

As used herein, the term "TLC" means thin layer chromatography.

"Transform", as used herein, refers to the introduction of a polynucleotide (single or double stranded DNA, RNA, or a combination thereof) into a living cell by any means. Transformation may be accomplished by a variety of methods, including, but not limited to, electroporation, polyethylene glycol mediated uptake, particle bombardment, agrotransformation, and the like. This process may result in transient or stable expression of the transformed polynucleotide. By "stably transformed" is meant that the sequence of interest is integrated into a replicon in the cell, such as a chromosome or episome. Transformed cells encompass not only the end product of a transformation process, but also the progeny thereof which retain the polynucleotide of interest.

For the purposes of the invention, "transgenic" refers to any cell, spore, tissue or part, that contains all or part of at least one recombinant polynucleotide. In many cases, all or part of the recombinant polynucleotide is stably integrated into a chromosome or stable extra-chromosomal element, so that it is passed on to successive generations.

As used herein, the term "transposase" refers to an enzyme that catalyzes transposition. Preferred transposons are described in WO 00/55346, PCT/US00/07317, and U.S. Ser. No. 09/658859.

As used herein, the term "transposition" refers to a complex genetic rearrangement process involving the movement or copying of a polynucleotide (transposon) from one location and insertion into another, often within or between a genome or genomes, or DNA constructs such as plasmids, bacmids, and cosmids.

As used herein, the term "transposon" (also known as a "transposable element", "transposable genetic element", "mobile element", or "jumping gene") refers to a mobile DNA element such as those, for example, described in WO00/55346, PCT/US00/07317, and U.S. Ser. No. 09/658859. Transposons can disrupt gene expression or cause deletions and inversions, and hence affect both the genotype and phenotype of the organisms concerned. The mobility of transposable elements has long been used in genetic manipulation, to introduce genes or other information into the genome of certain model systems.

As used herein, the term "Tween 20" means sorbitan mono-9-octadecenoate poly(oxy-1,1-ethanediyl).

As used in this disclosure, the term "viability" of an organism refers to the ability of an organism to demonstrate growth under conditions appropriate for said organism, or to demonstrate an active cellular function. Some examples of active cellular functions include respiration as measured by gas evolution, secretion of proteins and/or other compounds, dye exclusion, mobility, dye oxidation, dye reduction, pigment production, changes in medium acidity, and the like.

The present inventors have discovered that disruption of the AAR1 gene and/or gene product inhibits the pathogenicity of *Magnaporthe grisea*. Thus, the inventors are the first to demonstrate that α-Aminoadipate Reductase is a target for antibiotics, preferably antifungals.

Accordingly, the invention provides methods for identifying compounds that inhibit AAR1 gene expression or biological activity of its gene product(s). Such methods include ligand binding assays, assays for enzyme activity, cell-based assays, and assays for AAR1 gene expression. Any compound that is a ligand for α-Aminoadipate Reductase may have antibiotic activity. For the purposes of the invention, "ligand" refers to a molecule that will bind to a site on a polypeptide. The compounds identified by the methods of the invention are useful as antibiotics.

Thus, in one embodiment, the invention provides a method for identifying a test compound as a candidate for an antibiotic, comprising:

a) contacting a α-Aminoadipate Reductase polypeptide with said test compound; and b) detecting the presence or absence of binding between said test compound and said α-Aminoadipate Reductase polypeptide;

wherein binding indicates that said test compound is a candidate for an antibiotic.

The α-Aminoadipate Reductase protein may have the amino acid sequence of a naturally occurring α-Aminoadipate Reductase found in a fungus, animal, plant, or microorganism, or may have an amino acid sequence derived from a naturally occurring sequence. Preferably the α-Aminoadipate Reductase is a fungal α-Aminoadipate Reductase. The cDNA (SEQ ID NO: 1) encoding the α-Aminoadipate Reductase protein, the genomic DNA (SEQ ID NO: 2) encoding the protein, and the polypeptide (SEQ ID NO: 3) can be found herein.

By "fungal α-Aminoadipate Reductase" is meant an enzyme that can be found in at least one fungus, and which catalyzes the interconversion of L-2-Aminoadipate and NADPH and ATP with L-2-Aminoadipate 6-semialdehyde, NADP+, AMP, pyrophosphate, and $H_2O$. The α-Aminoadipate Reductase may be from any of the fungi, including ascomycota, zygomycota, basidiomycota, chytridiomycota, and lichens.

In one embodiment, the α-Aminoadipate Reductase is a Magnaporthe α-Aminoadipate Reductase. Magnaporthe species include, but are not limited to, *Magnaporthe rhizophila, Magnaporthe salvinii, Magnaporthe grisea* and *Magnaporthe poae* and the imperfect states of Magnaporthe in the genus Pyricularia. Preferably, the Magnaporthe α-Aminoadipate Reductase is from *Magnaporthe grisea.*

In various embodiments, the α-Aminoadipate Reductase can be from Powdery Scab (*Spongospora subterranea*), Grey Mould (*Botrytis cinerea*), White Rot (*Armillaria mellea*), Heartrot Fungus (*Ganoderma adspersum*), Brown-Rot (*Piptoporus betulinus*), Corn Smut (*Ustilago maydis*), Heartrot (*Polyporus squamosus*), Gray Leaf Spot (*Cercospora zeae-maydis*), Honey Fungus (*Armillaria gallica*), Root rot (*Armillaria luteobubalina*), Shoestring Rot (*Armillaria ostoyae*), Banana Anthracnose Fungus (*Colletotrichum musae*), Apple-rotting Fungus (*Monilinia

*fructigena*), Apple-rotting Fungus (*Penicillium expansum*), Clubroot Disease (*Plasmodiophora brassicae*), Potato Blight (*Phytophthora infestans*), Root pathogen (*Heterobasidion annosum*), Take-all Fungus (*Gaeumannomyces graminis*), Dutch Elm Disease (*Ophiostoma ulmi*), Bean Rust (*Uromyces appendiculatus*), Northern Leaf Spot (*Cochliobolus carbonum*), Milo Disease (*Periconia circinata*), Southern Corn Blight (*Cochliobolus heterostrophus*), Leaf Spot (*Cochliobolus lunata*), Brown Stripe (*Cochliobolus stenospilus*), Panama disease (*Fusarium oxysporum*), Wheat Head Scab Fungus (*Fusarium graminearum*), Cereal Foot Rot (*Fusarium culmorum*), Potato Black Scurf (*Rhizoctonia solani*), Wheat Black Stem Rust (*Puccinia graminis*), White mold (*Sclerotinia sclerotiorum*), and the like.

Fragments of an α-Aminoadipate Reductase polypeptide may be used in the methods of the invention, preferably if the fragments include an intact or nearly intact epitope that occurs on the biologically active wildtype α-Aminoadipate Reductase. The fragments comprise at least 10 consecutive amino acids of an α-Aminoadipate Reductase. Preferably, the fragment comprises at least 15, 20, 25, 30, 35, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, or at least 1180 consecutive amino acids residues of an α-Aminoadipate Reductase. In one embodiment, the fragment is from a Magnaporthe α-Aminoadipate Reductase. Preferably, the fragment contains an amino acid sequence conserved among fungal α-Aminoadipate Reductases.

Polypeptides having at least 50% sequence identity with a fungal α-Aminoadipate Reductase are also useful in the methods of the invention. Preferably, the sequence identity is at least 60%, more preferably the sequence identity is at least 70%, most preferably the sequence identity is at least 80% or 90 or 95 or 99%, or any integer from 60–100% sequence identity in ascending order.

In addition, it is preferred that the polypeptide has at least 10% of the activity of a fungal α-Aminoadipate Reductase. More preferably, the polypeptide has at least 25%, at least 50%, at least 75% or at least 90% of the activity of a fungal α-Aminoadipate Reductase. Most preferably, the polypeptide has at least 10%, at least 25%, at least 50%, at least 75% or at least 90% of the activity of the *M. grisea* α-Aminoadipate Reductase protein.

Thus, in another embodiment, the invention provides a method for identifying a test compound as a candidate for a fungicide, comprising:

a) contacting said test compound with at least one polypeptide selected from the group consisting of: a polypeptide having at least ten consecutive amino acids of a fungal α-Aminoadipate Reductase, a polypeptide having at least 50% sequence identity with a fungal α-Aminoadipate Reductase, and a polypeptide having at least 10% of the activity thereof; and b) detecting the presence and/or absence of binding between said test compound and said polypeptide; wherein binding indicates that said test compound is a candidate for an antibiotic.

Any technique for detecting the binding of a ligand to its target may be used in the methods of the invention. For example, the ligand and target are combined in a buffer. Many methods for detecting the binding of a ligand to its target are known in the art, and include, but are not limited to the detection of an immobilized ligand-target complex or the detection of a change in the properties of a target when it is bound to a ligand. For example, in one embodiment, an array of immobilized candidate ligands is provided. The immobilized ligands are contacted with an α-Aminoadipate Reductase protein or a fragment or variant thereof, the unbound protein is removed and the bound α-Aminoadipate Reductase is detected. In a preferred embodiment, bound α-Aminoadipate Reductase is detected using a labeled binding partner, such as a labeled antibody. In a variation of this assay, α-Aminoadipate Reductase is labeled prior to contacting the immobilized candidate ligands. Preferred labels include fluorescent or radioactive moieties. Preferred detection methods include fluorescence correlation spectroscopy (FCS) and FCS-related confocal nanofluorimetric methods.

Once a compound is identified as a candidate for an antibiotic, it can be tested for the ability to inhibit α-Aminoadipate Reductase enzymatic activity. The compounds can be tested using either in vitro or cell based assays. Alternatively, a compound can be tested by applying it directly to a fungus or fungal cell, or expressing it therein, and monitoring the fungus or fungal cell for changes or decreases in growth, development, viability, pathogenicity, or alterations in gene expression. Thus, in one embodiment, the invention provides a method for determining whether a compound identified as an antibiotic candidate by an above method has antifungal activity, further comprising: contacting a fungus or fungal cells with said antifungal candidate and detecting a decrease in the growth, viability, or pathogenicity of said fungus or fungal cells.

By decrease in growth, is meant that the antifungal candidate causes at least a 10% decrease in the growth of the fungus or fungal cells, as compared to the growth of the fungus or fungal cells in the absence of the antifungal candidate. By a decrease in viability is meant that at least 20% of the fungal cells, or portion of the fungus contacted with the antifungal candidate are nonviable. Preferably, the growth or viability will be decreased by at least 40%. More preferably, the growth or viability will be decreased by at least 50%, 75% or at least 90% or more. Methods for measuring fungal growth and cell viability are known to those skilled in the art. By decrease in pathogenicity, is meant that the antifungal candidate causes at least a 10% decrease in the disease caused by contact of the fungal pathogen with its host, as compared to the disease caused in the absence of the antifungal candidate. Preferably, the disease will be decreased by at least 40%. More preferably, the disease will be decreased by at least 50%, 75% or at least 90% or more. Methods for measuring fungal disease are well known to those skilled in the art, and include such metrics as lesion formation, lesion size, sporulation, respiratory failure, and/or death.

The ability of a compound to inhibit α-Aminoadipate Reductase activity can be detected using in vitro enzymatic assays in which the disappearance of a substrate or the appearance of a product is directly or indirectly detected. α-Aminoadipate Reductase catalyzes the irreversible or reversible reaction L-2-Aminoadipate and NADPH and ATP=L-2-Aminoadipate 6-semialdehyde, NADP+, AMP, pyrophosphate, and $H_2O$ (see FIG. 1). Methods for detection of L-2-Aminoadipate, L-2-Aminoadipate 6-semialdehyde, NADP+, NADPH, AMP, ATP, $H_2O$ and/or pyrophosphate, include spectrophotometry, mass spectroscopy, thin layer chromatography (TLC) and reverse phase HPLC.

Thus, the invention provides a method for identifying a test compound as a candidate for an antibiotic, comprising either:

a) contacting L-2-Aminoadipate and NADPH and ATP with an α-Aminoadipate Reductase;

b) contacting L-2-Aminoadipate and NADPH and ATP with α-Aminoadipate Reductase and said test compound; and c) determining the change in concentration for at least one of the following: L-2-Aminoadipate, L-2-Aminoadipate 6-semialdehyde, NADP+, NADPH, AMP, ATP, H$_2$O and/or pyrophosphate.

wherein a change in concentration for any of the above substances indicates that said test compound is a candidate for an antibiotic.

or, a) contacting L-2-Aminoadipate 6-semialdehyde, NADP+, AMP, pyrophosphate, and H$_2$O with an α-Aminoadipate Reductase;

b) contacting L-2-Aminoadipate 6-semialdehyde, NADP+, AMP, pyrophosphate, and H$_2$O with an α-Aminoadipate Reductase and said test compound; and c) determining the change in concentration for at least one of the following: L-2-Aminoadipate, L-2-Aminoadipate 6-semialdehyde, NADP+, NADPH, AMP, ATP, H$_2$O and/or pyrophosphate.

wherein a change in concentration for any of the above substances indicates that said test compound is a candidate for an antibiotic.

Enzymatically active fragments of a fungal α-Aminoadipate Reductase are also useful in the methods of the invention. For example, a polypeptide comprising at least 100 consecutive amino acid residues of a fungal α-Aminoadipate Reductase may be used in the methods of the invention. In addition, a polypeptide having at least 50%, 60%, 70%, 80%, 90%, 95% or at least 98% sequence identity with a fungal α-Aminoadipate Reductase may be used in the methods of the invention. Most preferably, the polypeptide has at least 50% sequence identity with a fungal α-Aminoadipate Reductase and at least 10%, 25%, 75% or at least 90% of the activity thereof.

Thus, the invention provides a method for identifying a test compound as a candidate for a fungicide, comprising:

a) contacting L-2-Aminoadipate and NADPH and ATP with a polypeptide selected from the group consisting of: a polypeptide having at least 50% sequence identity with an α-Aminoadipate Reductase, a polypeptide having at least 50% sequence identity with an α-Aminoadipate Reductase and having at least 10% of the activity thereof, and a polypeptide comprising at least 100 consecutive amino acids of an α-Aminoadipate Reductase b) contacting L-2-Aminoadipate and NADPH and ATP with said polypeptide and said test compound; and c) determining the change in concentration for at least one of the following: L-2-Aminoadipate, L-2-Aminoadipate 6-semialdehyde, NADP+, NADPH, AMP, ATP, H$_2$O and/or pyrophosphate.

wherein a change in concentration for any of the above substances indicates that said test compound is a candidate for an antibiotic.

or, a) contacting L-2-Aminoadipate 6-semialdehyde, NADP+, AMP, pyrophosphate, and H$_2$O with a polypeptide selected from the group consisting of: a polypeptide having at least 50% sequence identity with an α-Aminoadipate Reductase , a polypeptide having at least 50% sequence identity with an α-Aminoadipate Reductase and at least 10% of the activity thereof, and a polypeptide comprising at least 100 consecutive amino acids of an α-Aminoadipate Reductase b) contacting L-2-Aminoadipate 6-semialdehyde, NADP+, AMP, pyrophosphate, and H$_2$O, with said polypeptide and said test compound; and c) determining the change in concentration for at least one of the following, L-2-Aminoadipate, L-2-Aminoadipate 6-semialdehyde, NADP+, NADPH, AMP, ATP, H$_2$O and/or pyrophosphate;

wherein a change in concentration for any of the above substances indicates that said test compound is a candidate for an antibiotic.

For the in vitro enzymatic assays, α-Aminoadipate Reductase protein and derivatives thereof may be purified from a fungus or may be recombinantly produced in and purified from an archael, bacterial, fungal, or other eukaryotic cell culture. Preferably these proteins are produced using an *E. coli*, yeast, or filamentous fungal expression system. Methods for the purification of α-Aminoadipate Reductase may be described in Jaklitsch and Kubicek (Jaklitsch, W. M. and C. P. Kubicek (1990) Biochem J 269: 247–53 (PMID: 2115771)). Other methods for the purification of α-Aminoadipate Reductase proteins and polypeptides are known to those skilled in the art.

As an alternative to in vitro assays, the invention also provides cell based assays. In one embodiment, the invention provides a method for identifying a test compound as a candidate for a antibiotic, comprising:

a) measuring the expression of an α-Aminoadipate Reductase in a cell, cells, tissue, or an organism in the absence of said compound;

b) contacting said cell, cells, tissue, or organism with said test compound and measuring the expression of said α-Aminoadipate Reductase in said cell, cells, tissue, or organism;

c) comparing the expression of α-Aminoadipate Reductase in steps (a) and (b);

wherein a lower expression in the presence of said test compound indicates that said compound is a candidate for an antibiotic.

Expression of α-Aminoadipate Reductase can be measured by detecting the AAR1 primary transcript or mRNA, α-Aminoadipate Reductase polypeptide, or α-Aminoadipate Reductase enzymatic activity. Methods for detecting the expression of RNA and proteins are known to those skilled in the art. See, for example, *Current Protocols in Molecular Biology* Ausubel et al., eds., Greene Publishing and Wiley-Interscience, New York, 1995. The method of detection is not critical to the invention. Methods for detecting AAR1 RNA include, but are not limited to amplification assays such as quantitative reverse transcriptase-PCR, and/or hybridization assays such as Northern analysis, dot blots, slot blots, in-situ hybridization, transcriptional fusions using an AAR1 promoter fused to a reporter gene, DNA assays, and microarray assays.

Methods for detecting protein expression include, but are not limited to, immunodetection methods such as Western blots, ELISA assays, polyacrylamide gel electrophoresis, mass spectroscopy, and enzymatic assays. Also, any reporter gene system may be used to detect AAR1 protein expression. For detection using gene reporter systems, a polynucleotide encoding a reporter protein is fused in frame with AAR1, so as to produce a chimeric polypeptide. Methods for using reporter systems are known to those skilled in the art.

Chemicals, compounds or compositions identified by the above methods as modulators, preferably inhibitors, of AAR1 expression or activity can then be used to control fungal growth. Diseases such as rusts, mildews, and blights spread rapidly once established. Fungicides are thus routinely applied to growing and stored crops as a preventive measure, generally as foliar sprays or seed dressings. For example, compounds that inhibit fungal growth can be applied to a fungus or expressed in a fungus, in order to prevent fungal growth. Thus, the invention provides a method for inhibiting fungal growth, comprising contacting a fungus with a compound identified by the methods of the invention as having antifungal activity.

Antifungals and antifungal inhibitor candidates identified by the methods of the invention can be used to control the growth of undesired fungi, including ascomycota, zygomycota, basidiomycota, chytridiomycota, and lichens.

Examples of undesired fungi include, but are not limited to Powdery Scab (*Spongospora subterranea*), Grey Mould (*Botrytis cinerea*), White Rot (*Armillaria mellea*), Heartrot Fungus (*Ganoderma adspersum*), Brown-Rot (*Piptoporus betulinus*), Corn Smut (*Ustilago maydis*), Heartrot (*Polyporus squamosus*), Gray Leaf Spot (*Cercospora zeae-maydis*), Honey Fungus (*Armillaria gallica*), Root rot (*Armillaria luteobubalina*), Shoestring Rot (*Armillaria ostoyae*), Banana Anthracnose Fungus (*Colletotrichum musae*), Apple-rotting Fungus (*Monilinia fructigena*), Apple-rotting Fungus (*Penicillium expansum*), Clubroot Disease (*Plasmodiophora brassicae*), Potato Blight (*Phytophthora infestans*), Root pathogen (*Heterobasidion annosum*), Take-all Fungus (*Gaeumannomyces graminis*), Dutch Elm Disease (*Ophiostoma ulmi*), Bean Rust (*Uromyces appendiculatus*), Northern Leaf Spot (*Cochliobolus carbonum*), Milo Disease (*Periconia circinata*), Southern Corn Blight (*Cochliobolus heterostrophus*), Leaf Spot (*Cochliobolus lunata*), Brown Stripe (*Cochliobolus stenospilus*), Panama disease (*Fusarium oxysporum*), Wheat Head Scab Fungus (*Fusarium graminearum*), Cereal Foot Rot (*Fusarium culmorum*), Potato Black Scurf (*Rhizoctonia solani*), Wheat Black Stem Rust (*Puccinia graminis*), White mold (*Sclerotinia sclerotiorum*), diseases of animals such as infections of lungs, blood, brain, skin, scalp, nails or other tissues (*Aspergillus fumigatus* Aspergillus sp. Fusraium sp., Trichophyton sp., Epidermophyton sp., and Microsporum sp., and the like).

Also provided is a method of screening for an antibiotic by determining whether a test compound is active against the gene identified (SEQ ID NO: 1 or SEQ ID NO: 2), its gene product (SEQ ID NO: 3), or the biochemical pathway or pathways it functions on.

In one particular embodiment, the method is performed by providing an organism having a first form of the gene corresponding to either SEQ ID NO: 1 or SEQ ID NO: 2, either a normal form, a mutant form, a homologue, or a heterologous AAR1 gene that performs a similar function as AAR1. The first form of AAR1 may or may not confer a growth conditional phenotype, i.e., a lysine requiring phenotype, and/or a hypersensitivity or hyposensitivity phenotype on the organism having that altered form. In one particular embodiment a mutant form contains a transposon insertion. A comparison organism having a second form of an AAR1, different from the first form of the gene is also provided, and the two organisms are separately contacted with a test compound. The growth of the two organisms in the presence of the test compound is then compared.

Thus, in one embodiment, the invention provides a method for identifying a test compound as a candidate for an antibiotic, comprising:
  a) providing cells having one form of an α-Aminoadipate Reductase gene, and providing comparison cells having a different form of an α-Aminoadipate Reductase gene,
  b) contacting said cells and said comparison cells with a test compound and determining the growth of said cells and comparison cells in the presence of the test compound,
  wherein a difference in growth between said cells and said comparison cells in the presence of said test compound indicates that said test compound is a candidate for an antibiotic.

It is recognized in the art that the optional determination of the growth of said first organism and said comparison second organism in the absence of any test compounds may be performed to control for any inherent differences in growth as a result of the different genes. It is also recognized that any combination of two different forms of an AAR1 gene, including normal genes, mutant genes, homologues, and functional homologues may be used in this method. Growth and/or proliferation of an organism is measured by methods well known in the art such as optical density measurements, and the like. In a preferred embodiment the organism is *Magnaporthe grisea*.

Conditional lethal mutants may identify particular biochemical and/or genetic pathways given that at least one identified target gene is present in that pathway. Knowledge of these pathways allows for the screening of test compounds as candidates for antibiotics as inhibitors of the substrates, products and enzymes of the pathway. Pathways known in the art may be found at the Kyoto Encyclopedia of Genes and Genomes and in standard biochemistry texts (Lehninger, A., D. Nelson, et al. (1993) *Principles of Biochemistry.* New York, Worth Publishers).

Thus, in one embodiment, the invention provides a method for screening for test compounds acting against the biochemical and/or genetic pathway or pathways in which AAR1 functions, comprising:

a) providing cells having one form of a gene in the lysine biochemical and/or genetic pathway and providing comparison cells having a different form of said gene.
b) contacting said cells and comparison cells with a said test compound,
c) determining the growth of said cells and comparison cells in the presence of said test compound.

wherein a difference in growth between said cells and said comparison cells in the presence of said compound indicates that said compound is a candidate for an antibiotic.

The use of multi-well plates for screening is a format that readily accommodates multiple different assays to characterize various compounds, concentrations of compounds, and fungal strains in varying combinations and formats. Certain testing parameters for the screening method can significantly affect the identification of growth inhibitors, and thus can be manipulated to optimize screening efficiency and/or reliability. Notable among these factors are variable sensitivities of different mutants, increasing hypersensitivity with increasingly less permissive conditions, an apparent increase in hypersensitivity with increasing compound concentration, and other factors known to those in the art.

Conditional lethal mutants may identify particular biochemical and/or genetic pathways given that at least one identified target gene is present in that pathway. Knowledge of these pathways allows for the screening of test compounds as candidates for antibiotics. Pathways known in the art may be found at the Kyoto Encyclopedia of Genes and Genomes and in standard biochemistry texts (Lehninger, A., D. Nelson, et al. (1993) *Principles of Biochemistry*. New York, Worth Publishers). Thus, in one embodiment, the invention provides a method for screening for test compounds acting against the biochemical and/or genetic pathway or pathways in which AAR1 functions, comprising:

(a) providing paired growth media; comprising a first medium and a second medium, wherein said second medium contains a higher level of lysine than said first medium;

(b) contacting an organism with said test compound;

(c) inoculating said first and second media with said organism; and (d) determining the growth of said organism;

wherein a difference in growth of the organism between said first and second media indicates that said test compound is a candidate for an antibiotic.

It is recognized in the art that the optional determination of the growth of said organism in the paired media in the absence of any test compounds may be performed to control for any inherent differences in growth as a result of the different media. Growth and/or proliferation of an organism is measured by methods well known in the art such as optical density measurements, and the like. In a preferred embodiment, the organism is *Magnaporthe grisea*.

EXPERIMENTAL

Example 1

Construction of Plasmids with a Transposon Containing a Selectable Marker

Construction of Sif transposon: Sif was constructed using the GPS3 vector from the GPS-M mutagenesis system from New England Biolabs, Inc. (Beverly, Mass.) as a backbone. This system is based on the bacterial transposon Tn7. The following manipulations were done to GPS3 according to Sambrook et al. (1989) *Molecular Cloning, a Laboratory Manual,* Cold Spring Harbor Laboratory Press. The kanamycin resistance gene (npt) contained between the Tn7 arms was removed by EcoRV digestion. The bacterial hygromycin B phosphotransferase (hph) gene (Gritz and Davies (1983) Gene 25: 179–88 (PMID: 6319235)) under control of the *Aspergillus nidulans* trpC promoter and terminator (Mullaney et al. (1985) Mol Gen Genet 199: 37–45 (PMID: 3158796)) was cloned by a HpaI/EcoRV blunt ligation into the Tn7 arms of the GPS3 vector yielding pSif1. Excision of the ampicillin resistance gene (bla) from pSif1 was achieved by cutting pSif1 with XmnI and BglI followed by a T4 DNA polymerase treatment to remove the 3' overhangs left by the BglI digestion and religation of the plasmid to yield pSif. Top 10F' electrocompetent *E. coli* cells (Invitrogen) were transformed with ligation mixture according to manufacturer's recommendations. Transformants containing the Sif transposon were selected on LB agar (Sambrook et al. (1989) *Molecular Cloning, a Laboratory Manual,* Cold Spring Harbor Laboratory Press.) containing 50 ug/ml of hygromycin B (Sigma Chem. Co., St. Louis, Mo.).

Example 2

Construction of a Cosmid Library Containing Fungal Genes and a Selectable Marker Cosmid libraries were constructed in the pcosKA5 vector (Hamer et al. (2001) Proc Natl Acad Sci USA 98: 5110–15 (PMID: 11296265)) as described in Sambrook et al. (1989) *Molecular Cloning, a Laboratory Manual,* Cold Spring Harbor Laboratory Press. Cosmid libraries were quality checked by pulsed-field gel electrophoresis, restriction digestion analysis, and PCR identification of single genes.

Example 3

Construction of Cosmids with Transposon Inserted into Fungal Genes

Sif Transposition into a Cosmid: Transposition of Sif into the cosmid framework was carried out as described by the GPS-M mutagenesis system (New England Biolabs, Inc.). Briefly, 2 ul of the 10×GPS buffer, 70 ng of supercoiled pSIF, 8–12 μg of target cosmid DNA were mixed and taken to a final volume of 20 ul with water. 1 ul of transposase (TnsABC) was added to the reaction and incubated for 10 minutes at 37° C. to allow the assembly reaction to happen. After the assembly reaction 1 ul of start solution was added to the tube, mixed well and incubated for 1 hour at 37° C. followed by heat inactivation of the proteins at 75° C. for 10 min. Destruction of the remaining untransposed pSif was done by PISceI digestion at 37° C. for 2 hours followed by 10 min incubation at 75° C. to inactivate the proteins. Transformation of Top10F' electrocompetent cells (Invitrogen) was done according to manufacturers recommendations. Sif-containing cosmid transformants were selected by growth on LB agar plates containing 50 ug/ml of hygromycin B (Sigma Chem. Co.) and 100 ug/ml of Ampicillin (Sigma Chem. Co.).

Example 4

High Throughput Preparation and Verification of Insertion of Transposon into Fungal Genes

*E. coli* strains containing cosmids with transposon insertions were picked to 96 well growth blocks (Beckman Co.) containing 1.5 ml of TB (Terrific Broth, Sambrook et al. (1989) *Molecular Cloning, a Laboratory Manual,* Cold Spring Harbor Laboratory Press) supplemented with 50 ug/ml of ampicillin. Blocks were incubated with shaking at 37 C overnight. *E. coli* cells were pelleted by centrifugation and cosmids were isolated by a modified alkaline lysis method (Marra et al. (1997) Genome Res 7: 1072–84 (PMID: 9371743)). DNA quality was checked by electrophoresis on agarose gels. Cosmids were sequenced using primers from the ends of each transposon and commercial dideoxy sequencing kits (Big Dye Terminators, Perkin Elmer Co.). Sequencing reactions were analyzed on an ABI377 DNA sequencer (Perkin Elmer Co.).

DNA sequences adjacent to the site of the insertion were collected and used to search DNA and protein databases using the BLAST algorithms (Altschul et al. (1997) Nucleic Acids Res 25: 3389–3402 (PMID: 9254694)). A single insertion of SIF into the *Magnaporthe grisea* AAR1 gene was chosen for further analysis. This construct was designated cpgmra0015019g12 and it contains the SIF transposon approximately between amino acids 678 and 679 relative to the *Neurospora crassa* homologue (total length—1174 amino acids, GENBANK: 9367248 of accession number AL389890).

Example 5

Preparation of Cosmid DNA and Transformation of the Fungus *Magnaporthe grisea*

Cosmid DNA from the AAR1 transposon tagged cosmid clone was prepared using QIAGEN Plasmid Maxi Kit (QIAGEN), and digested by PI-PspI (New England Biolabs, Inc.). Fungal electro-transformation was performed essentially as described (Wu et al. (1997) MPMI 10: 700–708). Briefly, M. grisea strain Guy 11 was grown in complete liquid media (Talbot et al. (1993) Plant Cell 5: 1575–1590 (PMID: 8312740)) shaking at 120 rpm for 3 days at 25° C. in the dark. Mycelia was harvested and washed with sterile $H_2O$ and digested with 4 mg/ml beta-glucanase (InterSpex) for 4–6 hours to generate protoplasts. Protoplasts were collected by centrifugation and resuspended in 20% sucrose at the concentration of $2 \times 10^8$ protoplasts/ml. 50 ul protoplast suspension was mixed with 10–20 ug of the cosmid DNA and pulsed using Gene Pulser II (BioRad) set with the following parameters: resistance 200 ohm, capacitance 25 uF, voltage 0.6 kV. Transformed protoplasts were regenerated in complete agar media (CM, Talbot et al. (1993) Plant Cell 5: 1575–1590 (PMID: 8312740)) with the addition of 20% sucrose for one day, then overlayed with CM agar media containing hygromycin B (250 ug/ml) to select transformants. Transformants were screened for homologous recombination events in the target gene by PCR (Hamer et al. (2001) Proc Natl Acad Sci USA 98: 5110–15 (PMID: 11296265)). Two independent strains were identified and are hereby referred to as KO1-1 and KO1-11, respectively.

Example 6

Effect of Transposon Insertion on Magnaporthe Pathogenicity

The target fungal strains, KO1-1 and KO1-11, obtained in Example 5 and the wild type strain, Guy11, were subjected to a pathogenicity assay to observe infection over a 1-week period. Rice infection assays were performed using Indian rice cultivar CO39 essentially as described in Valent et al. ((1991) Genetics 127: 87–101 (PMID: 2016048)). All three strains were grown for spore production on complete agar media. Spores were harvested and the concentration of spores adjusted for whole plant inoculations. Two-week-old seedlings of cultivar CO39 were sprayed with 12 ml of conidial suspension ($5\times10^4$conidia per ml in 0.01% Tween-20 (Polyoxyethylensorbitan monolaureate) solution). The inoculated plants were incubated in a dew chamber at 27° C. in the dark for 36 hours, and transferred to a growth chamber (27° C. 12 hours/21° C. 12 hours 70% humidity) for an additional 5.5 days. Leaf samples were taken at 3, 5, and 7 days post-inoculation and examined for signs of successful infection (i.e. lesions). FIG. 2 shows the effects of AAR1 gene disruption on Magnaporthe infection at five days post-inoculation.

Example 7

Verification of Gene Function by Analysis of Nutritional Requirements

The fungal strains, KO1-1 and KO1-11, containing the AAR1 disrupted gene obtained in Example 5 were analyzed for their nutritional requirement for lysine using the PM5 phenotype microarray from Biolog, Inc. (Hayward, Calif.). The PM5 plate tests for the auxotrophic requirement for 94 different metabolites. The inoculating fluid consists of 0.05% Phytagel, 0.03% Pluronic F68, 1% glucose, 23.5 mM $NaNO_3$, 6.7 mM KCl, 3.5 mM $Na_2SO_4$, 11 mM $KH_2PO_4$, 0.01% p-iodonitrotetrazolium violet, 0.1 mM $MgCl_2$, 1.0 mM $CaCl_2$ and trace elements. Final concentrations of trace elements are: 7.6 $\mu$M $ZnCl_2$, 2.5 $\mu$M $MnCl_2.4H_2O$, 1.8 $\mu$M $FeCl_2.4H_2O$, 0.71 $\mu$M $CoCl_2.6H_2O$, 64 $\mu$M $CuCl_2.2H_2O$, 0.62 $\mu$M $Na_2MoO_4$, 18 $\mu$M $H_3BO_3$. pH adjusted to 6.0 with NaOH. Spores for each strain were harvested into the inoculating fluid. The spore concentrations were adjusted to $2\times10^5$ spores/ml. 100 $\mu$l of spore suspension were deposited into each well of the microtiter plates. The plates were incubated at 25° C. for 7 days. Optical density (OD) measurements at 490 nm and 750 nm were taken daily. The $OD_{490}$ measures the extent of tetrazolium dye reduction and the level of growth, and $OD_{750}$ measures growth only. Turbidity=$OD_{490}$+$OD_{750}$. Data confirming the annotated gene function is presented as a graph of Turbidity vs. Time showing both the mutant fungi and the wild-type control in the absence (FIG. 3A) and presence (FIG. 3B) of L-lysine.

Example 8

Cloning and Expression Strategies, Extraction and Purification of α-Aminoadipate Reductase Protein The following protocol may be employed to obtain a purified α-Aminoadipate Reductase protein.

Cloning and Expression Strategies:

An AAR1 cDNA gene can be cloned into *E. coli* (pET vectors-Novagen), Baculovirus (Pharmingen) and Yeast (Invitrogen) expression vectors containing His/fusion protein tags. Evaluate the expression of recombinant protein by SDS-PAGE and Western blot analysis.

Extraction:

Extract recombinant protein from 250 ml cell pellet in 3 ml of extraction buffer By sonicating 6 times, with 6 sec pulses at 4° C. Centrifuge extract at 15000×g for 10 min and collect supernatant. Assess biological activity of the recombinant protein by activity assay.

Purification:

Purify recombinant protein by Ni-NTA affinity chromatography (Qiagen).

Purification protocol: perform all steps at 4° C.:

Use 3 ml Ni-beads (Qiagen)

Equilibrate column with the buffer

Load protein extract

Wash with the equilibration buffer

Elute bound protein with 0.5 M imidazole

Example 9

Assays for Testing Binding of Test Compounds to α-Aminoadipate Reductase

The following protocol may be employed to identify test compounds that bind to the α-Aminoadipate Reductase protein.

Purified full-length α-Aminoadipate Reductase polypeptide with a His/fusion protein tag (Example 8) is bound to a HisGrab™ Nickel Coated Plate (Pierce, Rockford, Ill.) following manufacturer's instructions.

Buffer conditions are optimized (e.g. ionic strength or pH, Jaklitsch, W. M. and C. P. Kubicek (1990) Biochem J 269: 247–53 (PMID: 2115771)) for binding of radiolabeled $^{14}$C-α-Aminoadipic acid (Sigma-Aldrich Co.) to the bound AAR 1.

Screening of test compounds is performed by adding test compound and $^{14}$C-α-Aminoadipic acid (Sigma-Aldrich Co.) to the wells of the HisGrab™ plate containing bound AAR1.

The wells are washed to remove excess labeled ligand and scintillation fluid (Scintiverse®, Fisher Scientific) is added to each well.

The plates are read in a microplate scintillation counter.

Candidate compounds are identified as wells with lower radioactivity as compared to control wells with no test compound added.

Additionally, a purified polypeptide comprising 10–50 amino acids from the *M. grisea* α-Aminoadipate Reductase is screened in the same way. A polypeptide comprising 10–50 amino acids is generated by subcloning a portion of the AAR1 gene into a protein expression vector that adds a His-Tag when expressed (see Example 8). Oligonucleotide primers are designed to amplify a portion of the AAR1 gene using the polymerase chain reaction amplification method. The DNA fragment encoding a polypeptide of 10–50 amino acids is cloned into an expression vector, expressed in a host organism and purified as described in Example 8 above.

Test compounds that bind AAR1 are further tested for antibiotic activity. *M. grisea* is grown as described for spore production on oatmeal agar media (Talbot et al. (1993) Plant Cell 5: 1575–1590 (PMID: 8312740)). Spores are harvested into minimal media (Talbot et al. (1993) Plant Cell 5: 1575–1590 (PMID: 8312740)) to a concentration of $2\times10^5$ spores/ml and the culture is divided. The test compound is added to one culture to a final concentration of 20–100 μg/ml. Solvent only is added to the second culture. The plates are incubated at 25° C. for seven days and optical density measurements at 590 nm are taken daily. The growth curves of the solvent control sample and the test compound sample are compared. A test compound is an antibiotic candidate if the growth of the culture containing the test compound is less than the growth of the control culture.

Example 10

Assays for Testing Inhibitors or Candidates for Inhibition of α-Aminoadipate Reductase Activity The enzymatic activity of α-Aminoadipate Reductase is determined in the presence and absence of candidate compounds in a suitable reaction mixture, such as described by Gray and Bhattacharjee (Gray, G S and Bhattacharjee, J K (1976) Can J Microbiol 22: 1664–7 (PMID: 10066)), or Jaklitsch, W. M. and C. P. Kubicek (1990) Biochem J 269: 247–53 (PMID: 2115771). Candidate compounds are identified when a decrease in products or a lack of decrease in substrates is detected with the reaction proceeding in either direction.

Additionally, the enzymatic activity of a polypeptide comprising 10–50 amino acids from the *M. grisea* α-Aminoadipate Reductase is determined in the presence and absence of candidate compounds in a suitable reaction mixture, such as described by Gray and Bhattacharjee (Gray, G S and Bhattacharjee, J K (1976) Can J Microbiol 22: 1664–7 (PMID: 10066)), or Jaklitsch, W. M. and C. P. Kubicek (1990) Biochem J 269: 247–53 (PMID: 2115771). A polypeptide comprising 10–50 amino acids is generated by subcloning a portion of the AAR1 gene into a protein expression vector that adds a His-Tag when expressed (see Example 8). Oligonucleotide primers are designed to amplify a portion of the AAR1 gene using polymerase chain reaction amplification method. The DNA fragment encoding a polypeptide of 10–50 amino acids is cloned into an expression vector, expressed and purified as described in Example 8 above.

Test compounds identified as inhibitors of AAR1 activity are further tested for antibiotic activity. *Magnaporthe grisea* fungal cells are grown under standard fungal growth conditions that are well known and described in the art. *M. grisea* is grown as described for spore production on oatmeal agar media (Talbot et a. (1993) Plant Cell 5: 1575–1590 (PMID: 8312740)). Spores are harvested into minimal media (Talbot et al. (1993) Plant Cell 5: 1575–1590 (PMID: 8312740)) to a concentration of $2\times10^5$ spores/ml and the culture is divided. The test compound is added to one culture to a final concentration of 20–100 μg/ml. Solvent only is added to the second culture. The plates are incubated at 25° C. for seven days and optical density measurements at 590 nm are taken daily. The growth curves of the solvent control sample and the test compound sample are compared. A test compound is an antibiotic candidate if the growth of the culture containing the test compound is less than the growth of the control culture.

Example 11

Assays for Testing Compounds or Candidates for Compounds That Alter the Expression of an α-Aminoadipate Reductase Gene

*Magnaporthe grisea* fungal cells are grown under standard fungal growth conditions that are well known and described in the art. Wild-type *M. grisea* spores are harvested from cultures grown on complete agar or oatmeal agar media after growth for 10–13 days in the light at 25° C. using a moistened cotton swab. The concentration of spores is determined using a hemacytometer and spore suspensions are prepared in a minimal growth medium to a concentration of $2\times10^5$ spores per ml. 25 ml cultures are prepared to which test compounds will be added at various concentrations. A culture with no test compound present is included as a control. The cultures are incubated at 25° C. for 3 days after which test compound or solvent only control is added. The cultures are incubated an additional 18 hours. Fungal mycelia is harvested by filtration through Miracloth (CalBiochem®, La Jolla, Calif.), washed with water and frozen in liquid nitrogen. Total RNA is extracted with TRIZOL® Reagent using the methods provided by the manufacturer (Life Technologies, Rockville, Md.). Expression is analyzed by Northern analysis of the RNA samples as described (Sambrook et al. (1989) *Molecular Cloning, a Laboratory Manual,* Cold Spring Harbor Laboratory Press) using a radiolabeled fragment of the AAR1 gene as a probe. Test compounds resulting in a reduced level of AAR1 mRNA relative to the untreated control sample are identified as candidate antibiotic compounds.

Example 12

In Vivo Cell Based Assay Screening Protocol with a Fungal Strain Containing a Mutant Form of α-Aminoadipate Reductase with No Activity

*Magnaporthe grisea* fungal cells containing a mutant form of the AAR1 gene which abolishes enzyme activity, such as a gene containing a transposon insertion (see Examples 4 and 5), are grown under standard fungal growth conditions that are well known and described in the art. *Magnaporthe grisea* spores are harvested from cultures grown on complete agar medium containing 4 mM L-lysine (Sigma-Aldrich Co.) after growth for 10–13 days in the light at 25° C. using a moistened cotton swab. The concentration of spores is determined using a hemacytometer and spore suspensions are prepared in a minimal growth medium containing 100 μM L-lysine to a concentration of $2\times10^5$ spores per ml. Approximately $4\times10^4$ spores are added to each well of 96-well plates to which a test compound is added (at varying concentrations). The total volume in each well is 200 μl. Wells with no test compound present (growth control), and wells without cells are included as controls (negative control). The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 13

In Vivo Cell Based Assay Screening Protocol with a Fungal Strain Containing a Mutant Form of α-Aminoadipate Reductase with Reduced Activity

*Magnaporthe grisea* fungal cells containing a mutant form of the AAR1 gene, such as a promoter truncation that reduces expression, are grown under standard fungal growth conditions that are well known and described in the art. A promoter truncation is made by deleting a portion of the promoter upstream of the transcription start site using standard molecular biology techniques that are well known and described in the art (Sambrook et al. (1989) *Molecular Cloning, a Laboratory Manual*, Cold Spring Harbor Laboratory Press). *Magnaporthe grisea* spores are harvested from cultures grown on complete agar medium containing 4 mM L-lysine (Sigma-Aldrich Co.) after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores are added to each well of 96-well plates to which a test compound is added (at varying concentrations). The total volume in each well is 200 µl. Wells with no test compound present (growth control), and wells without cells are included as controls (negative control). The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild-type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 14

In Vivo Cell Based Assay Screening Protocol with a Fungal Strain Containing a Mutant Form of a Lysine Biosynthetic Gene with No Activity

*Magnaporthe grisea* fungal cells containing a mutant form of a gene in the lysine biosynthetic pathway (e.g. HCS1 (E.C. 4.1.3.21)) are grown under standard fungal growth conditions that are well known and described in the art. *Magnaporthe grisea* spores are harvested from cultures grown on complete agar medium containing 4 mM L-lysine (Sigma-Aldrich Co.) after growth for 10–13 days in the light at 25° C. using a moistened cotton swab. The concentration of spores is determined using a hemacytometer and spore suspensions are prepared in a minimal growth medium containing 100 µM L-lysine to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 µl. Wells with no test compound present, and wells without cells are included as controls. The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild type cells are compared. Compounds that show differential growth inhibition between the mutant and the wild-type are identified as potential antifungal compounds. Similar protocols may be found in Kirsch and DiDomenico ((1994) Biotechnology 26: 177–221 (PMID: 7749303)).

Example 15

In Vivo Cell Based Assay Screening Protocol with a Fungal Strain Containing a Mutant Form of a Lysine Biosynthetic Gene with Reduced Activity

*Magnaporthe grisea* fungal cells containing a mutant form of a gene in the lysine biosynthetic pathway (e.g. HCS1 (E.C. 4.1.3.21)), such as a promoter truncation that reduces expression, are grown under standard fungal growth conditions that are well known and described in the art. A promoter truncation is made by deleting a portion of the promoter upstream of the transcription start site using standard molecular biology techniques that are well known and described in the art (Sambrook et al. (1989) *Molecular Cloning, a Laboratory Manual*, Cold Spring Harbor Laboratory Press). *Magnaporthe grisea* fungal cells containing a mutant form of are grown under standard fungal growth conditions that are well known and described in the art. *Magnaporthe grisea* spores are harvested from cultures grown on complete agar medium containing 4 mM L-lysine (Sigma-Aldrich Co.) after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 µl. Wells with no test compound present, and wells without cells are included as controls. The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 16

In Vivo Cell Based Assay Screening Protocol with a Fungal Strain Containing a Fungal AAR1 and a Second Fungal Strain Containing a Heterologous AAR1 Gene Wild-type *Magnaporthe grisea* fungal cells and *M. grisea* fungal cells lacking a functional AAR1 gene and containing an AAR1 gene from *Penicillium chrysogenum* (Genbank accession Y13967, 56% sequence identity) are grown under standard fungal growth conditions that are well known and described in the art. A *M. grisea* strain carrying a heterologous AAR1 gene is made as follows:

- A *M. grisea* strain is made with a nonfunctional AAR1 gene, such as one containing a transposon insertion in the native gene (see Examples 4 and 5).
- A construct containing a heterologous AAR1 gene is made by cloning the AAR1 gene from *Penicillium chrysogenum* into a fungal expression vector containing a trpC promoter and terminator (e.g. pCB1003, Carroll et al. (1994) Fungal Gen News Lett 41: 22) using standard molecular biology techniques that are well known and described in the art (Sambrook et al. (1989) *Molecular Cloning, a Laboratory Manual,* Cold Spring Harbor Laboratory Press).
- The said construct is used to transform the *M. grisea* strain lacking a functional AAR1 gene (see Example 5). Transformants are selected on minimal agar medium lacking L-lysine. Only transformants carrying a functional AAR1 gene will grow.

Wild-type strains of *Magnaporthe grisea* and strains containing a heterologous form of AAR1 are grown under standard fungal growth conditions that are well known and described in the art. *Magnaporthe grisea* spores are harvested from cultures grown on complete agar medium after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 μl. Wells with no test compound present, and wells without cells are included as controls. The plates are incubated at 25° C. for seven days and optical density measurements at 590nm are taken daily. The effect of each compound on the wild-type and heterologous fungal strains is measured against the growth control and the percent of inhibition is calculated as the $OD_{590}$ (fungal strain plus test compound)/$OD_{590}$ (growth control)×100. The percent of growth inhibition as a result of a test compound on the wild-type and heterologous fungal strains are compared. Compounds that show differential growth inhibition between the wild-type and heterologous strains are identified as potential antifungal compounds with specificity to the native or heterologous AAR1 gene products. Similar protocols may be found in Kirsch and DiDomenico ((1994) Biotechnology 26: 177–221 (PMID: 7749303)).

Example 17

Pathway Specific In Vivo Assay Screening Protocol

*Magnaporthe grisea* fungal cells are grown under standard fungal growth conditions that are well known and described in the art. Wild-type *M. grisea* spores are harvested from cultures grown on oatmeal agar media after growth for 10–13 days in the light at 25° C. using a moistened cotton swab. The concentration of spores is determined using a hemocytometer and spore suspensions are prepared in a minimal growth medium and a minimal growth medium containing 4 mM L-lysine (Sigma-Aldrich Co.) to a concentration of $2\times10^5$ spores per ml. The minimal growth media contains carbon, nitrogen, phosphate, and sulfate sources, and magnesium, calcium, and trace elements (for example, see inoculating fluid in Example 7). Spore suspensions are added to each well of a 96-well microtiter plate (approximately $4\times10^4$ spores/well). For each well containing a spore suspension in minimal media, an additional well is present containing a spore suspension in minimal medium containing 4 mM L-lysine. Test compounds are added to wells containing spores in minimal media and minimal media containing L-lysine. The total volume in each well is 200 μl. Both minimal media and L-lysine containing media wells with no test compound are provided as controls. The plates are incubated at 25° C. for seven days and optical density measurements at 590 nm are taken daily. A compound is identified as a candidate for an antibiotic acting against the lysine biosynthetic pathway when the observed growth in the well containing minimal media is less than the observed growth in the well containing L-lysine as a result of the addition of the test compound. Similar protocols may be found in Kirsch and DiDomenico ((1994) Biotechnology 26: 177–221 (PMID: 7749303)).

While the foregoing describes certain embodiments of the invention, it will be understood by those skilled in the art that variations and modifications may be made and still fall within the scope of the invention. The foregoing examples are intended to exemplify various specific embodiments of the invention and do not limit its scope in any manner.

What is claimed is:

1. A method for identifying a test compound as a candidate for an antibiotic, comprising:
   a) contacting a Magnaporthe α-Aminoadipate Reductase polypeptide with said test compound; and
   b) detecting the presence or absence of binding between said test compound and said Magnaporthe α-Aminoadipate Reductase polypeptide; wherein binding indicates that said test compound is a candidate for an antibiotic.

2. The method of claim 1, wherein said Magnaporthe α-Aminoadipate Reductase polypeptide is SEQ ID NO: 3.

3. A method for identifying a test compound as a candidate for an antibiotic, comprising:
   a) contacting L-2-Aminoadipate and NADPH and ATP with an α-Aminoadipate Reductase;

b) contacting L-2-Aminoadipate and NADPH and ATP with α-Aminoadipate Reductase and said test compound; and c) determining the change in concentration for at least one of the following: L-2-Aminoadipate, L-2-Aminoadipate 6-semialdehyde, NADP+, NADPH, AMP, ATP, $H_2O$ and/or pyrophosphate; wherein a change in concentration for any of the above substances between steps (a) and (b) indicates that said test compound is a candidate for an antibiotic.

4. The method of claim 3, wherein said α-Aminoadipate Reductase is a fungal α-Aminoadipate Reductase.

5. The method of claim 3, wherein said α-Aminoadipate Reductase is a Magnaporthe α-Aminoadipate Reductase.

6. The method of claim 3, wherein said α-Aminoadipate Reductase is SEQ ID NO: 3.

7. A method for determining whether a compound identified as an antibiotic candidate by the method of claim 3, has antifungal activity, further comprising:
contacting a fungus or fungal cells with said antibiotic candidate and detecting a decrease in growth, viability, or pathogenicity of said fungus or fungal cells.

8. A method for identifying a test compound as a candidate for an antibiotic, comprising:
   a) contacting L-2-Aminoadipate 6-semialdehyde, NADP+, AMP, pyrophosphate, and H$_2$O with an α-Aminoadipate Reductase;
   b) contacting L-2-Aminoadipate 6-semialdehyde, NADP+, AMP, pyrophosphate, and H$_2$O with an α-Aminoadipate Reductase and said test compound; and
   c) determining the change in concentration for at least one of the following: L-2-Aminoadipate, L-2-Aminoadipate 6-semialdehyde, NADP+, NADPH, AMP, ATP, H$_2$O and/or pyrophosphate; wherein a change in concentration for any of the above substances between steps (a) and (b) indicates that said test compound is a candidate for an antibiotic.

9. The method of claim 8, wherein said α-Aminoadipate Reductase is a fungal α-Aminoadipate Reductase.

10. The method of claim 8, wherein said α-Aminoadipate Reductase is a Magnaporthe α-Aminoadipate Reductase.

11. The method of claim 8, wherein said α-Aminoadipate Reductase is SEQ ID NO: 3.

12. A method for determining whether a compound identified as an antibiotic candidate by the method of claim 8 has antifungal activity, further comprising:
contacting a fungus or fungal cells with said antibiotic candidate and detecting a decrease in growth, viability, or pathogenicity of said fungus or fungal cells.

13. A method for identifying a test compound as a candidate for an antibiotic, comprising:
   a) contacting L-2-Aminoadipate and NADPH and ATP with a polypeptide selected from the group consisting of: a polypeptide having at least 50% sequence identity with an α-Aminoadipate Reductase, a polypeptide having at least 50% sequence identity with an α-Aminoadipate Reductase and having at least 10% of the activity thereof, and a polypeptide comprising at least 100 consecutive amino acids of an α-Aminoadipate Reductase
   b) contacting L-2-Aminoadipate and NADPH and ATP with said polypeptide and said test compound; and
   c) determining the change in concentration for at least one of the following: L-2-Aminoadipate, L-2-Aminoadipate 6-semialdehyde, NADP+, NADPH, AMP, ATP, H$_2$O and/or pyrophosphate; wherein a change in concentration for any of the above substances between steps (a) and (b) indicates that said test compound is a candidate for an antibiotic.

14. A method for identifying a test compound as a candidate for an antibiotic, comprising:
   a) contacting L-2-Aminoadipate 6-semialdehyde, NADP+, AMP, pyrophosphate, and H$_2$O with a polypeptide selected from the group consisting of: a polypeptide having at least 50% sequence identity with an α-Aminoadipate Reductase, a polypeptide having at least 50% sequence identity with an α-Aminoadipate Reductase and at least 10% of the activity thereof, and a polypeptide comprising at least 100 consecutive amino acids of an α-Aminoadipate Reductase
   b) contacting L-2-Aminoadipate 6-semialdehyde, NADP+, AMP, pyrophosphate, and H$_2$O with said polypeptide and said test compound; and
   c) determining the change in concentration for at least one of the following: L-2-Aminoadipate, L-2-Aminoadipate 6-semialdehyde, NADP+, NADPH, AMP, ATP, H$_2$O and/or pyrophosphate; wherein a change in concentration for any of the above substances between steps (a) and (b) indicates that said test compound is a candidate for an antibiotic.

15. A method for identifying a test compound as a candidate for an antibiotic, comprising:
   a) measuring the expression of a Magnaporthe α-Aminoadipate Reductase in a cell, cells, tissue, or an organism in the absence of said compound;
   b) contacting said cell, cells, tissue, or organism with said test compound and measuring the expression of said Magnaporthe α-Aminoadipate Reductase in said fungus or fungal cell;
   c) comparing the expression of Magnaporthe α-Aminoadipate Reductase in steps (a) and (b); wherein a lower expression in the presence of said test compound indicates that said compound is a candidate for an antibiotic.

16. The method of claim 15, wherein said Magnaporthe α-Aminoadipate Reductase is SEQ ID NO: 3.

17. A method for identifying a test compound as a candidate for an antibiotic, comprising:
   a) providing cells having one form of an α-Aminoadipate Reductase gene, and providing comparison cells having a different form of an α-Aminoadipate Reductase gene,
   b) contacting said cells and said comparison cells with a test compound and determining the growth of said cells and comparison cells in the presence of the test compound;
wherein a difference in growth between said cells and said comparison cells in the presence of said compound indicates that said compound is a candidate for an antibiotic.

18. The method of claim 17 wherein the cells are fungal cells.

19. The method of claim 17 wherein the cells are Magnaporthe cells.

20. The method of claim 17 wherein said form and said comparison form of the α-Aminoadipate Reductase are fungal α-Aminoadipate Reductases.

21. The method of claim 17, wherein at least one form is a Magnaporthe α-Aminoadipate Reductase.

22. The method of claim 17 wherein said form and said comparison form of the α-Aminoadipate Reductase are non-fungal α-Aminoadipate Reductases.

23. The method of claim 17 wherein one form of the α-Aminoadipate Reductase is a fungal α-Aminoadipate Reductase, and the other form is a non-fungal α-Aminoadipate Reductase.

24. A method for identifying a test compound as a candidate for an antibiotic, comprising:
   a) providing cells having one form of a gene in the lysine biochemical and/or genetic pathway and providing comparison cells having a different form of said gene,
   b) contacting said cells and comparison cells with a said test compound,
   c) determining the growth of said cells and comparison cells in the presence of said test compound; wherein a difference in growth between said cells and said comparison cells in the presence of said compound indicates that said compound is a candidate for an antibiotic.

25. The method of claim 24 wherein the cells are fungal cells.

26. The method of claim 24 wherein the cells are Magnaporthe cells.

27. The method of claim 24 wherein said form and said comparison form of the lysine biosynthesis gene are fungal lysine biosynthesis genes.

28. The method of claim 24, wherein at least one form is a Magnaporthe lysine biosynthesis gene.

29. The method of claim 24 wherein said form and said comparison form of the lysine biosynthesis genes are non-fungal lysine biosynthesis genes.

30. The method of claim 24 wherein one form of the lysine biosynthesis gene is a fungal lysine biosynthesis gene, and the other form is a non-fungal lysine biosynthesis gene.

31. A method for determining whether a test compound identified as an antibiotic candidate by the method of claim 24 has antifungal activity, further comprising:
    contacting a fungus or fungal cells with said antibiotic candidate and detecting a decrease in growth, viability, or pathogenicity of said fungus or fungal cells.

32. A method for identifying a test compound as a candidate for an antibiotic, comprising:
    (a) providing paired growth media; comprising a first medium and a second medium, wherein said second medium contains a higher level of lysine than said first medium;
    (b) contacting an organism with said test compound;
    (c) inoculating said first and second media with said organism; and
    (d) determining the growth of said organism; wherein a difference in growth of the organism between said first and second media indicates that said test compound is a candidate for an antibiotic.

33. The method of claim 32, wherein said organism is a fungus.

34. The method of claim 32, wherein said organism is Magnaporthe.

35. An isolated polynucleotide comprising a nucleotide sequence that encodes a polypeptide of SEQ ID NO: 3.

36. The polynucleotide of claim 35 comprising the nucleotide sequence of SEQ ID NO: 1.

37. An expression cassette comprising the polynucleotide of claim 36.

38. The isolated polynucleotide of claim 37 comprising a nucleotide sequence of at least 50 to at least 95% sequence identity to SEQ ID NO: 1.

39. A polypeptide consisting essentially of the amino acid sequence of SEQ ID NO: 3.

40. A polypeptide comprising the amino acid sequence of SEQ ID NO: 3.

* * * * *

SEQUENCE LISTING

```
<160> NUMBER OF SEQ ID NOS: 3

<210> SEQ ID NO 1
<211> LENGTH: 3567
<212> TYPE: DNA
<213> ORGANISM: Magnaporthe grisea

<400> SEQUENCE: 1
```

-continued

| | |
|---|---|
| atggcgcatc agctccccga cccaacggtc gacctcgact ggtctggcta cgtcggcgcc | 60 |
| attcatgaga tctttgccac taatgcccag aagcacccgg agcgggtgtg cgtgatcgag | 120 |
| acagagtcct ccgaggcacc ggaaaggata tttacctaca agcagatctt tgaggcgtca | 180 |
| aatgtcctgg cgcactacct acatgatgct ggagtcacta atggcgatgt ggtcatgatc | 240 |
| tgggcgcata ggtcagttga cctggttgtc agcatcatgg gtgttcttgc tgccggagct | 300 |
| acattcagtg tccttgaccc attatacccg ccatctcgtc agcagatcta cctcgaagta | 360 |
| tccggcccga ccgcccttgt acaaatcgcg cgcgccaccg acgaggccgg cccgttggcc | 420 |
| cccctcgtgc gcaggtacat cgacgaggag ctgaagctga aggccgaggt tccgtcacta | 480 |
| cgcatcggcg acgatggcca cctctcgggt ggagagatca acggcgctga tgttttttgcc | 540 |
| agcgtgcgcg gcaaggcatc ctcaccgcct gcagacattg aggtcggacc cgactcgaac | 600 |
| cccacactta gcttcacgtc aggctcggaa ggccggccta agggcgtgct ggtcgacac | 660 |
| tacagcttgg ccaagtattt tcgatggatg gccgagacgt tcggcatggg cgaagagagc | 720 |
| cgcttcacac tgctctcggg tatcgcgcac gaccctgtgc agcgagatat cttcacgcca | 780 |
| ctgtacctgg gcgcgcgcct actggtgccg tccaaggaga atattgcaca cgagcgtcta | 840 |
| gcagagtggt tcaagcgctt tgaaccaaca gtgacacacc tgacgccggc catgggtcag | 900 |
| attttagtcg gcggcgctac cgcacagttc cctgccctga aaacagccta cttcgtcggc | 960 |
| gatgtgctga cgacgcgaga ctgccgcagt ctgcgtgagc tcgcggcaaa cgttgacatt | 1020 |
| gttaacatgt acgggacgac tgagacgagc agagctgtca gctactacaa gatcccgaac | 1080 |
| cgcgcctcag acccggactt tctggagaga ttgggcaagg acacaatccc tgctggaact | 1140 |
| ggcatggaaa acgttcagct tttggttgtc aaccgggaag ataggacaaa gctttgtggt | 1200 |
| atcggcgaag tgggcgagat ctacgtgcgt gcggctggtc tggctgaggg ctacaagggc | 1260 |
| gaccccgctt gaacgaaca gaagttcctg atgaactggt tcgtggataa caacaagtgg | 1320 |
| gttgaggcgg acagggtgca cccaaccaag gatgcggcat ggagaaagta ctacaagggc | 1380 |
| cctctcgaca ggctgtaccg cacaggtgac ctcggaaagt atttggattc gggcgatgtg | 1440 |
| gaatgcactg gtcgtgcaga cgatcaagtc aaaatcaggg gcttcaggat tgaactcaac | 1500 |
| gacattgaca gcaacctgag tcagagctcc ctcatcaggg actgcaagac gcttgtgcga | 1560 |
| agggacaaga acgaggagcc gaagctggtc agctacgttg tgcctgagct caagcaatgg | 1620 |
| ccccaatggc tcaagcttca tggctacgag gatgctgaag acgatgaggg cacgcaaatt | 1680 |
| ggagcaacca aggtatactt caagaggtat cgtcgtatgc aggctgagct tcgcgaccat | 1740 |
| ctcaagtcaa ggttgccgac ctacgccgtt cctagcatct tcattgtcct ggagaagctg | 1800 |
| ccattaaacc ccaacggcaa ggttgacaag cccaatctac cttttcccga tattgccgag | 1860 |
| caaaccgcgg aagcttcaag cgaggagatt gagcgatggg agtctttgac cgagactgag | 1920 |
| cgtgctgttg ccaccaggtg ggctgcgttg atccagggtc tgaacgaaaa gtcgatcgcg | 1980 |
| cccgataacc acttctttga cctcggcggt cacagtattc tggcacagca aatgctgctc | 2040 |
| gacgtgcgca agcagatggg tgctaatgtg tctatcaaca cccctttacga gaaccccacg | 2100 |
| cttgggcat tcagtcttca gattgacaag catcttggag cagccaatga tgctagcacc | 2160 |
| agccaagtcg aggatgaggc aaactcgtat gccaaggctc gtgatgatct cgttaagaaa | 2220 |
| cttccagcct catacaagac agcagatccg tcgtcgatcc gggcgtcatc cagacctacc | 2280 |
| atcttcctga ctggcgcaac gggtttcttg ggtgcctttt tgatccgcga tatcctgcag | 2340 |
| aggacgagcc gacagctgaa gctcatcgca cacgtgcgtg ccaaggacca aaaagcggcg | 2400 |

```
acagagcgtc tgacgcggtc actacagggc tacggtatct ggcgcgacga gtgggctggg      2460
cgcctttcct gcgtagtggg tgacctagcc aagccgcaac ttggtattga tcagcccaca      2520
tgggagcgcc tgtcgaacga ggtggacgta gttatccaca acggtgcgac agtccactgg      2580
gtgcgccgct ggcaagacat gctggccgcc aacgtcacat cgacaatcga ggccatgcgg      2640
ctgtgcaacg agggcaagcc aaagttgttc actttcgtca gctcaactag cgtcttggac      2700
actgagcact atgtgcagtt gtcggagagg caactgagca ccggccaagg cgccgtcccc      2760
gagtctgacg acctcgaagg cagtgccact ggcttgggta caggttacgg ccaaaccaag      2820
tggatctcgg agcagctcgt cagggaggcg ggccgacgcg gacttcgagg ctccgttgtc      2880
aggccaggct acattctggg agatttcgag tcgggatgtt ccaacacaga cgacttcctc      2940
attcgcttcc tcaagggctg tatccagctc ggcacgaggc cccgcattct caatactgtc      3000
aatgccgtgc ccgtcaacca cgttgcgcgt gttgttgtcg cggctggtct caaccctgta      3060
cccgtccagg gtaatgaagg tgtccacgtg gtccacgtta cgggccaccc gcgcctgcgg      3120
atgaacgagt atctctcgtt gcttgagttc tacggctaca aggtgcccga ggtgccgtat      3180
gattcatgga aggaggagct ggagcagtac gtgtctgcgg gcgcgggtgt cgagcgcgac      3240
caggagcagc acgcgctgct acctctcttc cacctctgta tctcggacct gcccgccaac      3300
actaaggcac ctgagcttga ggaccaaaac gctgtcgcgg tcctcaaggc ggacgctgag      3360
gcctggaccg ggctcgacga gagcgcgggc tacggcatcg gcaggggagga cgtcggaagg      3420 tacctccgct acctagccat gatcaagttt gtcccctggc ctacgtcgag gggcaggcct      3480
ttgcctgagg tcagcatcag cacggagcag gtggctgcta tgggtgcagg cgtcggtgga      3540
cgtggtggtg cgggtgcggg acagtga                                        3567
```

<210> SEQ ID NO 2
<211> LENGTH: 7586
<212> TYPE: DNA
<213> ORGANISM: Magnaporthe grisea

<400> SEQUENCE: 2

```
catcacgagt cagtttagga agcctggctc tgggagagct cccgcgccaa attgccccag       60
aaattaagca tccatgccaa gagcggcttc ccgatgtcgc aataccgaat gtcattgtgg      120
atcaattttt tttacattct gcagggatct aattgagctt tgaaaagtcg agtcaccgtc      180
accagagtta ctcactcttc ttttttttca gcaagcatct tggtgggctg ctggcttctt      240
gttttgcttg atgtctgtaa aagattcaat cgaggccagg ggcagtttta agtacatata      300
aactttgcaa aaagctaggg ttcacatacc agtcaacgca tacacactgg cgcagtagta      360
ccccgccaat tgtcccccat cacgataaat cgtcaccatg gcgcatcagc tccccgaccc      420
aacggtcgac ctcgactggt ctggctacgt cggcgccatt catgagatct ttgccactaa      480
tgcccagaag cacccggagc gggtgtgcgt gatcgagaca gagtcctccg aggcaccgga      540
aaggatattt acctacaagc agatctttga ggcgtcaaat gtcctggcgc actacctaca      600
tgatgctgga gtcactaatg gcgatgtggt catgatctgg gcgcataggt cagttgacct      660
ggttgtcagc atcatgggtg ttcttgtaag ctgcatcttc cctccctatg aacttgaccg      720
attccccgcc ttgtcttagc cagcactgtt tctccgagag aacggaaaca ctgacatgac      780
caaaaccatt cctaggctgc cggagctaca ttcagtgtcc ttgacccatt atacccgcca      840
tctcgtcagc agatctacct cgaagtatcc ggcccgaccg cccttgtaca aatcgcgcgc      900
```

-continued

```
gccaccgacg aggccggccc gttggccccc ctcgtgcgca ggtacatcga cgaggagctg    960
aagctgaagg ccgaggttcc gtcactacgc atcggcgacg atggccacct ctcgggtgga   1020
gagatcaacg cgctgatgt ttttgccagc gtgcgcggca aggcatcctc accgcctgca   1080
gacattgagg tcggacccga ctcgaacccc acacttagct tcacgtcagg ctcggaaggc   1140
cggcctaagg gcgtgcttgg tcgacactac agcttggcca agtattttcg atggatggcc   1200
gagacgttcg gcatgggcga agagagccgc ttcacactgc tctcgggtat cgcgcacgac   1260
cctgtgcagc gagatatctt cacgccactg tacctgggcg cgcgcctact ggtgccgtcc   1320
aaggagaata ttgcacacga gcgtctagca gagtggttca agcgctttga accaacagtg   1380
acacacctga cgccggccat gggtcagatt ttagtcggcg cgctaccgc acagttccct    1440 gccctgaaaa cagcctactt cgtcggcgat gtgctgacga cgcgagactg ccgcagtctg   1500
cgtgagctcg cggcaaacgt tgacattgtt aacatgtacg ggacgactga gacgagcaga   1560
gctgtcagct actacaagat cccgaaccgc gcctcagacc cggactttct ggagagattg   1620
ggcaaggaca caatccctgc tggaactggc atggaaaacg ttcagctttt ggttgtcaac   1680
cgggaagata ggacaaagct tgtggtatc ggcgaagtgg gcgagatcta cgtgcgtgcg    1740
gctggtctgg ctgagggcta caagggcgac cccgctttga cgaacagaa gttcctgatg    1800 aactggttcg tggataacaa caagtgggtt gaggcggaca gggtgcaccc aaccaaggat   1860
gcggcatgga gaaagtacta caagggcccc tcgacaggc tgtaccgcac aggtgacctc    1920
ggaaagtatt tggattcggg cgatgtgaa tgcactggtc gtgcagacga tcaagtcaaa    1980 atcagggct tcaggattga actcaacgac attgacagca acctgagtca gagctccctc    2040
atcagggact gcaagacgct tgtgcgaagg gacaagaacg aggagccgaa gctggtcagc   2100
tacgttgtgc ctgagctcaa gcaatggccc caatggctca gcttcatgg ctacgaggat    2160 gctgaagacg atgagggcac gcaaattgga gcaaccaagg tatacttcaa gaggtatcgt   2220
cgtatgcagg ctgagcttcg cgaccatctc aagtcaaggt tgccgaccta cgccgttcct   2280
agcatcttca ttgtcctgga gaagctgcca ttaaacccca acggcaaggt tgacaagccc   2340
aatctacctt ttcccgatat tgccgagcaa accgcggaag cttcaagcga ggagattgag   2400
cgatgggagt ctttgaccga gactgagcgt gctgttgcca ccaggtgggc tgcgttgatc   2460
cagggtctga acgaaaagtc gatcgcgccc gataaccact tctttgacct cggcggtcac   2520
agtattctgg cacagcaaat gctgctcgac gtgcgcaagc agatgggtgc taatgtgtct   2580
atcaacaccc tttacgagaa ccccacgctt ggggcattca gtcttcagat tgacaagcat   2640
cttggagcag ccaatgatgc tagcaccagc caagtcgagg atgaggcaaa ctcgtatgcc   2700
aaggctcgtg atgatctcgt taagaaactt ccagcctcat acaagacagc agatccgtcg   2760
tcgatccggg cgtcatccag acctaccatc ttcctgactg gcgcaacggg tttcttgggt   2820 gccttttga tccgcgatat cctgcagagg acgagccgac agctgaagct catcgcacac   2880
gtgcgtgcca aggaccaaaa agcggcgaca gagcgtctga cgcggtcact acagggctac   2940
ggtatctggc gcgacgagtg ggctgggcgc ctttcctgcg tagtgggtga cctagccaag   3000
ccgcaacttg gtattgatca gcccacatgg gagcgcctgt cgaacgaggt ggacgtagtt   3060
atccacaacg gtgcgacagt ccactggtg cgccgctggc aagacatgct ggccgccaac    3120
gtcacatcga caatcgaggc catgcggctg tgcaacgagg gcaagccaaa gttgttcact   3180
ttcgtcagct caactagcgt cttggacact gagcactatg tgcagttgtc ggagaggcaa   3240
ctgagcaccg gccaaggcgc cgtccccgag tctgacgacc tcgaaggcag tgccactggc   3300
```

```
ttgggtacag gttacggcca aaccaacatc acgagtcagt ttaggaagcc tggctctggg    3360
agagctcccg cgccaaattg ccccagaaat taagcatcca tgccaagagc ggcttcccga    3420
tgtcgcaata ccgaatgtca ttgtggatca atttttttta cattctgcag ggatctaatt    3480
gagctttgaa aagtcgagtc accgtcacca gagttactca ctcttctttt ttttcagcaa    3540
gcatcttggt gggctgctgg cttcttgttt tgcttgatgt ctgtaaaaga ttcaatcgag    3600
gccaggggca gttttaagta catataaact ttgcaaaaag ctagggttca cataccagtc    3660
aacgcataca cactggcgca gtagtacccc gccaattgtc ccccatcacg ataaatcgtc    3720
accatggcgc atcagctccc cgacccaacg gtcgacctcg actggtctgg ctacgtcggc    3780
gccattcatg agatctttgc cactaatgcc cagaagcacc ggagcgggt gtgcgtgatc    3840 gagacagagt cctccgaggc accggaaagg atatttacct acaagcagat ctttgaggcg    3900
tcaaatgtcc tggcgcacta cctacatgat gctggagtca ctaatggcga tgtggtcatg    3960
atctgggcgc ataggtcagt tgacctggtt gtcagcatca tgggtgttct tgtaagctgc    4020
atcttccctc cctatgaact tgaccgattc cccgccttgt cttagccagc actgtttctc    4080
cgagagaacg gaaacactga catgaccaaa accattccta ggctgccgga gctacattca    4140
gtgtccttga cccattatac cgccatctc gtcagcagat ctacctcgaa gtatccggcc    4200
cgaccgccct tgtacaaatc gcgcgcgcca ccgacgaggc cggcccgttg gccccctcg    4260 tgcgcaggta catcgacgag gagctgaagc tgaaggccga ggttccgtca ctacgcatcg    4320
gcgacgatgg ccacctctcg ggtggagaga tcaacggcgc tgatgttttt gccagcgtgc    4380
gcggcaaggc atcctcaccg cctgcagaca ttgaggtcgg acccgactcg aaccccacac    4440
ttagcttcac gtcaggctcg gaaggccggc ctaagggcgt gcttggtcga cactacagct    4500
tggccaagta ttttcgatgg atggccgaga cgttcggcat gggcgaagag agccgcttca    4560
cactgctctc gggtatcgcg cacgaccctg tgcagcgaga tatcttcacg ccactgtacc    4620
tgggcgcgcg cctactggtg ccgtccaagg agaatattgc acacgagcgt ctagcagagt    4680
ggttcaagcg ctttgaacca acagtgacac acctgacgcc ggccatgggt cagattttag    4740
tcggcggcgc taccgcacag ttccctgccc tgaaaacagc ctacttcgtc ggcgatgtgc    4800
tgacgacgcg agactgccgc agtctgcgtg agctcgcggc aaacgttgac attgttaaca    4860
tgtacgggac gactgagacg agcagagctg tcagctacta caagatcccg aaccgcgcct    4920
cagacccgga ctttctggag agattgggca aggacacaat ccctgctgga actggcatgg    4980
aaaacgttca gcttttggtt gtcaaccggg aagataggac aaagctttgt ggtatcggcg    5040
aagtgggcga gatctacgtg cgtgcggctg gtctggctga gggctacaag ggcgaccccg    5100
ctttgaacga acagaagttc ctgatgaact ggttcgtgga taacaacaag tgggttgagg    5160
cggacagggt gcacccaacc aaggatgcgg catggagaaa gtactacaag ggccctctcg    5220
acaggctgta ccgcacaggt gacctcggaa agtatttgga ttcgggcgat gtggaatgca    5280
ctggtcgtgc agacgatcaa gtcaaaatca ggggcttcag gattgaactc aacgacattg    5340
acagcaacct gagtcagagc tccctcatca gggactgcaa gacgcttgtg cgaagggaca    5400
agaacgagga gccgaagctg gtcagctacg ttgtgcctga gctcaagcaa tggccccaat    5460
ggctcaagct tcatggctac gaggatgctg aagacgatga gggcacgcaa attggagcaa    5520
ccaaggtata cttcaagagg tatcgtcgta tgcaggctga gcttcgcgac catctccaagt    5580 caaggttgcc gacctacgcc gttcctagca tcttcattgt cctggagaag ctgccattaa    5640
```

-continued

```
acccccaacgg caaggttgac aagcccaatc taccttttcc cgatattgcc gagcaaaccg   5700
cggaagcttc aagcgaggag attgagcgat gggagtcttt gaccgagact gagcgtgctg   5760
ttgccaccag gtgggctgcg ttgatccagg gtctgaacga aaagtcgatc gcgcccgata   5820
accacttctt tgacctcggc ggtcacagta ttctggcaca gcaaatgctg ctcgacgtgc   5880
gcaagcagat gggtgctaat gtgtctatca cacccttta cgagaacccc acgcttgggg   5940
cattcagtct tcagattgac aagcatcttg agcagccaa tgatgctagc accagccaag   6000
tcgaggatga ggcaaactcg tatgccaagg ctcgtgatga tctcgttaag aaacttccag   6060
cctcatacaa gacagcagat ccgtcgtcga tccgggcgtc atccagacct accatcttcc   6120
tgactggcgc aacgggtttc ttgggtgcct tttgatccg cgatatcctg cagaggacga   6180
gccgacagct gaagctcatc gcacacgtgc gtgccaagga ccaaaaagcg gcgacagagc   6240
gtctgacgcg gtcactacag ggctacggta tctggcgcga cgagtgggct gggcgccttt   6300
cctgcgtagt gggtgaccta gccaagccgc aacttggtat tgatcagccc acatgggagc   6360
gcctgtcgaa cgaggtggac gtagttatcc acaacggtgc gacagtccac tgggtgcgcc   6420
gctggcaaga catgctggcc gccaacgtca catcgacaat cgaggccatg cggctgtgca   6480
acgagggcaa gccaaagttg ttcactttcg tcagctcaac tagcgtcttg gacactgagc   6540
actatgtgca gttgtcggag aggcaactga gcaccggcca aggcgccgtc cccgagtctg   6600
acgacctcga aggcagtgcc actggcttgg gtacaggtta cggccaaacc aagtggatct   6660
cggagcagct cgtcagggag gcgggccgac gcggacttcg aggctccgtt gtcaggccag   6720
gctacattct gggagatttc gagtcgggat gttccaacac agacgacttc ctcattcgct   6780
tcctcaaggg ctgtatccag ctcggcacga ggccccgcat tctcaatact gtcaatgccg   6840
tgcccgtcaa ccacgttgcg cgtgttgttg tcgcggctgg tctcaacct gtacccgtcc   6900 agggtaatga agttgtccac gtggtccacg ttacgggcca cccgcgcctg cggatgaacg   6960
agtatctctc gttgcttgag ttctacggct acaaggtgcc cgaggtgccg tatgattcat   7020
ggaaggagga gctggagcag tacgtgtctg cgggcgcggg tgtcgagcgc gaccaggagc   7080
agcacgcgct gctacctctc ttccacctct gtatctcgga cctgcccgcc aacactaagg   7140
cacctgagct tgaggaccaa aacgctgtcg cggtcctcaa ggcggacgct gaggcctgga   7200
ccgggctcga cgagagcgcg ggctacggca tcggcaggga ggacgtcgga aggtacctcc   7260
gctacctagc catgatcaag tttgtcccct ggcctacgtc gaggggcagg cctttgcctg   7320
aggtcagcat cagcacggag caggtggctg ctatgggtgc aggcgtcggt ggacgtggtg   7380
gtgcgggtgc gggacagtga acgaaaagaa tggtggacgg ctagccatct gagtatatga   7440
ctgttttctt taaatgaatt ggtagctttg cttttttaaa aggtgcttgg tttggaattt   7500
aaagttgatt tctcgggcta aaaaaaaaaa aaaaaactcg agggggggcc cggtacccaa   7560
ttcgccctat agtgagtcgt attcaa                                        7586
```

<210> SEQ ID NO 3
<211> LENGTH: 1188
<212> TYPE: PRT
<213> ORGANISM: Magnaporthe grisea

<400> SEQUENCE: 3

```
Met Ala His Gln Leu Pro Asp Pro Thr Val Asp Leu Asp Trp Ser Gly
 1               5                  10                  15

Tyr Val Gly Ala Ile His Glu Ile Phe Ala Thr Asn Ala Gln Lys His
            20                  25                  30
```

```
Pro Glu Arg Val Cys Val Ile Glu Thr Glu Ser Ser Glu Ala Pro Glu
         35                  40                  45
Arg Ile Phe Thr Tyr Lys Gln Ile Phe Glu Ala Ser Asn Val Leu Ala
     50                  55                  60
His Tyr Leu His Asp Ala Gly Val Thr Asn Gly Asp Val Val Met Ile
 65              70                  75                      80
Trp Ala His Arg Ser Val Asp Leu Val Val Ser Ile Met Gly Val Leu
                 85                  90              95
Ala Ala Gly Ala Thr Phe Ser Val Leu Asp Pro Leu Tyr Pro Pro Ser
            100                 105             110
Arg Gln Gln Ile Tyr Leu Glu Val Ser Gly Pro Thr Ala Leu Val Gln
        115                 120             125
Ile Ala Arg Ala Thr Asp Glu Ala Gly Pro Leu Ala Pro Leu Val Arg
        130             135             140
Arg Tyr Ile Asp Glu Glu Leu Lys Leu Lys Ala Glu Val Pro Ser Leu
145             150             155                         160
Arg Ile Gly Asp Asp Gly His Leu Ser Gly Gly Glu Ile Asn Gly Ala
                165             170                 175
Asp Val Phe Ala Ser Val Arg Gly Lys Ala Ser Ser Pro Pro Ala Asp
            180             185             190
Ile Glu Val Gly Pro Asp Ser Asn Pro Thr Leu Ser Phe Thr Ser Gly
        195             200             205
Ser Glu Gly Arg Pro Lys Gly Val Leu Gly Arg His Tyr Ser Leu Ala
    210             215             220
Lys Tyr Phe Arg Trp Met Ala Glu Thr Phe Gly Met Gly Glu Glu Ser
225             230             235                         240
Arg Phe Thr Leu Leu Ser Gly Ile Ala His Asp Pro Val Gln Arg Asp
            245             250             255
Ile Phe Thr Pro Leu Tyr Leu Gly Ala Arg Leu Leu Val Pro Ser Lys
            260             265             270
Glu Asn Ile Ala His Glu Arg Leu Ala Glu Trp Phe Lys Arg Phe Glu
        275             280             285
Pro Thr Val Thr His Leu Thr Pro Ala Met Gly Gln Ile Leu Val Gly
    290             295             300
Gly Ala Thr Ala Gln Phe Pro Ala Leu Lys Thr Ala Tyr Phe Val Gly
305             310             315                         320
Asp Val Leu Thr Thr Arg Asp Cys Arg Ser Leu Arg Glu Leu Ala Ala
            325             330             335
Asn Val Asp Ile Val Asn Met Tyr Gly Thr Thr Glu Thr Ser Arg Ala
            340             345             350
Val Ser Tyr Tyr Lys Ile Pro Asn Arg Ala Ser Asp Pro Asp Phe Leu
        355             360             365
Glu Arg Leu Gly Lys Asp Thr Ile Pro Ala Gly Thr Gly Met Glu Asn
    370             375             380
Val Gln Leu Leu Val Val Asn Arg Glu Asp Arg Thr Lys Leu Cys Gly
385             390             395                         400
Ile Gly Glu Val Gly Glu Ile Tyr Val Arg Ala Ala Gly Leu Ala Glu
            405             410             415
Gly Tyr Lys Gly Asp Pro Ala Leu Asn Glu Gln Lys Phe Leu Met Asn
        420             425             430
Trp Phe Val Asp Asn Asn Lys Trp Val Glu Ala Asp Arg Val His Pro
    435             440             445
```

-continued

```
Thr Lys Asp Ala Ala Trp Arg Lys Tyr Lys Gly Pro Leu Asp Arg
450                 455                 460

Leu Tyr Arg Thr Gly Asp Leu Gly Lys Tyr Leu Asp Ser Gly Asp Val
465                 470                 475                 480

Glu Cys Thr Gly Arg Ala Asp Asp Gln Val Lys Ile Arg Gly Phe Arg
                485                 490                 495

Ile Glu Leu Asn Asp Ile Asp Ser Asn Leu Ser Gln Ser Ser Leu Ile
                500                 505                 510

Arg Asp Cys Lys Thr Leu Val Arg Arg Asp Lys Asn Glu Glu Pro Lys
                515                 520                 525

Leu Val Ser Tyr Val Val Pro Glu Leu Lys Gln Trp Pro Gln Trp Leu
530                 535                 540

Lys Leu His Gly Tyr Glu Asp Ala Glu Asp Glu Gly Thr Gln Ile
545                 550                 555                 560

Gly Ala Thr Lys Val Tyr Phe Lys Arg Tyr Arg Arg Met Gln Ala Glu
                565                 570                 575

Leu Arg Asp His Leu Lys Ser Arg Leu Pro Thr Tyr Ala Val Pro Ser
                580                 585                 590

Ile Phe Ile Val Leu Glu Lys Leu Pro Leu Asn Pro Asn Gly Lys Val
                595                 600                 605

Asp Lys Pro Asn Leu Pro Phe Pro Asp Ile Ala Glu Gln Thr Ala Glu
610                 615                 620

Ala Ser Ser Glu Glu Ile Glu Arg Trp Glu Ser Leu Thr Glu Thr Glu
625                 630                 635                 640

Arg Ala Val Ala Thr Arg Trp Ala Ala Leu Ile Gln Gly Leu Asn Glu
                645                 650                 655

Lys Ser Ile Ala Pro Asp Asn His Phe Phe Asp Leu Gly Gly His Ser
                660                 665                 670

Ile Leu Ala Gln Gln Met Leu Leu Asp Val Arg Lys Gln Met Gly Ala
                675                 680                 685

Asn Val Ser Ile Asn Thr Leu Tyr Glu Asn Pro Thr Leu Gly Ala Phe
                690                 695                 700

Ser Leu Gln Ile Asp Lys His Leu Gly Ala Ala Asn Asp Ala Ser Thr
705                 710                 715                 720

Ser Gln Val Glu Asp Glu Ala Asn Ser Tyr Ala Lys Ala Arg Asp Asp
                725                 730                 735

Leu Val Lys Lys Leu Pro Ala Ser Tyr Lys Thr Ala Asp Pro Ser Ser
                740                 745                 750

Ile Arg Ala Ser Ser Arg Pro Thr Ile Phe Leu Thr Gly Ala Thr Gly
                755                 760                 765

Phe Leu Gly Ala Phe Leu Ile Arg Asp Ile Leu Gln Arg Thr Ser Arg
770                 775                 780

Gln Leu Lys Leu Ile Ala His Val Arg Ala Lys Asp Gln Lys Ala Ala
785                 790                 795                 800

Thr Glu Arg Leu Thr Arg Ser Leu Gln Gly Tyr Gly Ile Trp Arg Asp
                805                 810                 815

Glu Trp Ala Gly Arg Leu Ser Cys Val Val Gly Asp Leu Ala Lys Pro
                820                 825                 830

Gln Leu Gly Ile Asp Gln Pro Thr Trp Glu Arg Leu Ser Asn Glu Val
                835                 840                 845

Asp Val Val Ile His Asn Gly Ala Thr Val His Trp Val Arg Arg Trp
850                 855                 860

Gln Asp Met Leu Ala Ala Asn Val Thr Ser Thr Ile Glu Ala Met Arg
```

-continued

```
865                 870                 875                 880
Leu Cys Asn Glu Gly Lys Pro Lys Leu Phe Thr Phe Val Ser Ser Thr
                885                 890                 895
Ser Val Leu Asp Thr Glu His Tyr Val Gln Leu Ser Glu Arg Gln Leu
            900                 905                 910
Ser Thr Gly Gln Gly Ala Val Pro Glu Ser Asp Asp Leu Glu Gly Ser
        915                 920                 925
Ala Thr Gly Leu Gly Thr Gly Tyr Gly Gln Thr Lys Trp Ile Ser Glu
    930                 935                 940
Gln Leu Val Arg Glu Ala Gly Arg Arg Gly Leu Arg Gly Ser Val Val
945                 950                 955                 960
Arg Pro Gly Tyr Ile Leu Gly Asp Phe Glu Ser Gly Cys Ser Asn Thr
                965                 970                 975
Asp Asp Phe Leu Ile Arg Phe Leu Lys Gly Cys Ile Gln Leu Gly Thr
            980                 985                 990
Arg Pro Arg Ile Leu Asn Thr Val  Asn Ala Val Pro Val  Asn His Val
        995                 1000                1005
Ala Arg Val Val Val Ala Ala  Gly Leu Asn Pro Val  Pro Val Gln
    1010                1015                1020
Gly Asn Glu Gly Val His Val  Val His Val Thr Gly  His Pro Arg
    1025                1030                1035
Leu Arg Met Asn Glu Tyr Leu  Ser Leu Leu Glu Phe  Tyr Gly Tyr
    1040                1045                1050
Lys Val Pro Glu Val Pro Tyr  Asp Ser Trp Lys Glu  Glu Leu Glu
    1055                1060                1065
Gln Tyr Val Ser Ala Gly Ala  Gly Val Glu Arg Asp  Gln Glu Gln
    1070                1075                1080
His Ala Leu Leu Pro Leu Phe  His Leu Cys Ile Ser  Asp Leu Pro
    1085                1090                1095
Ala Asn Thr Lys Ala Pro Glu  Leu Glu Asp Gln Asn  Ala Val Ala
    1100                1105                1110
Val Leu Lys Ala Asp Ala Glu  Ala Trp Thr Gly Leu  Asp Glu Ser
    1115                1120                1125
Ala Gly Tyr Gly Ile Gly Arg  Glu Asp Val Gly Arg  Tyr Leu Arg
    1130                1135                1140
Tyr Leu Ala Met Ile Lys Phe  Val Pro Trp Pro Thr  Ser Arg Gly
    1145                1150                1155
Arg Pro Leu Pro Glu Val Ser  Ile Ser Thr Glu Gln  Val Ala Ala
    1160                1165                1170
Met Gly Ala Gly Val Gly Gly  Arg Gly Gly Ala Gly  Ala Gly Gln
    1175                1180                1185
```